(12) United States Patent
Erlander et al.

(10) Patent No.: US 8,895,269 B2
(45) Date of Patent: *Nov. 25, 2014

(54) GENE EXPRESSION PROFILING FROM FFPE SAMPLES

(76) Inventors: Mark G. Erlander, Carlsbad, CA (US); Ranelle C. Salunga, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/205,563

(22) Filed: Aug. 8, 2011

(65) Prior Publication Data

US 2012/0245046 A1    Sep. 27, 2012

Related U.S. Application Data

(63) Continuation of application No. 12/855,577, filed on Aug. 12, 2010, now Pat. No. 8,012,688, which is a continuation of application No. 12/616,103, filed on Nov. 10, 2009, now Pat. No. 7,879,555, which is a continuation of application No. 12/111,745, filed on Apr. 29, 2008, now Pat. No. 7,723,039, which is a continuation of application No. 10/329,282, filed on Dec. 23, 2002, now Pat. No. 7,364,846.

(60) Provisional application No. 60/418,103, filed on Oct. 11, 2002.

(51) Int. Cl.
  *C12Q 1/68* (2006.01)
  *C12N 15/10* (2006.01)
  *G06F 19/20* (2011.01)

(52) U.S. Cl.
  CPC ............. *C12Q 1/6809* (2013.01); *G06F 19/20* (2013.01); *C12N 15/1096* (2013.01); *C12Q 2600/158* (2013.01)
  USPC ................... 435/91.51; 435/91.21; 435/6.11; 435/6.12

(58) Field of Classification Search
  None
  See application file for complete search history.

(56) References Cited

U.S. PATENT DOCUMENTS

| | | | |
|---|---|---|---|
| 5,698,410 A * | 12/1997 | Burstein et al. | 435/7.23 |
| 5,932,451 A * | 8/1999 | Wang et al. | 435/91.21 |
| 6,248,535 B1 * | 6/2001 | Danenberg et al. | 435/6.12 |
| 6,596,482 B1 * | 7/2003 | Jones | 435/6.12 |
| 7,364,846 B2 * | 4/2008 | Erlander et al. | 435/6.12 |
| 7,723,039 B2 * | 5/2010 | Erlander et al. | 435/6.12 |
| 7,879,555 B2 * | 2/2011 | Erlander et al. | 435/6.12 |
| 8,012,688 B2 * | 9/2011 | Erlander et al. | 435/6.12 |
| 2002/0081597 A1 * | 6/2002 | Lowe et al. | 435/6 |

OTHER PUBLICATIONS

Karsten et al. (Nucleic Acids Res. Jan. 15, 2002;30(2):E4).*

* cited by examiner

*Primary Examiner* — Christopher M. Babic
*Assistant Examiner* — Aaron Priest
(74) *Attorney, Agent, or Firm* — Logue PC

(57) ABSTRACT

Methods and compositions relating to the generation and use of gene expression data from tissue samples that have been fixed and embedded are provided. The data can be electronically stored and implemented as well as used to augment diagnosis and treatment of diseases.

17 Claims, 8 Drawing Sheets

M   1 day   4 days   8 days   frozen
Days in formalin

GENE EXPRESSION PROFILING FROM FFPE SAMPLES

CROSS-REFERENCE TO RELATED APPLICATIONS

This application claims benefit of priority from U.S. Provisional Application 60/418,103 filed 11 Oct. 2002, which is hereby incorporated in its entirety as if fully set forth.

TECHNICAL FIELD

The present invention relates to the amplification of expressed nucleic acid molecules in samples that have been fixed by formalin, formaldehyde or paraformaldehyde. The samples may be those embedded in wax and/or stored for extended periods of time.

The invention also relates to the use of the amplified nucleic acid molecules to determine gene expression levels in said samples and the correlation thereof to various diseases and conditions. The information on gene expression levels may be electronically stored and used to assist in the diagnosis and treatment of disease.

BACKGROUND ART

Gene expression analyses of various tumor types (breast, lung, prostate and colon) have revealed that there exist numerous subtypes of tumors within each anatomically defined cancer. Furthermore, in some of these studies different subtypes have been linked to a particular prognosis. For example, Wigle et al, (1) and Beer et al., (2) demonstrate the existence of particular clusters of genes that are correlated with different disease-free survivals in non-small cell lung cancer. These reports establish that the molecular "make-up" of tumors, as defined by gene expression profiles, has a direct correlation to clinical endpoints such as disease free survival. These retrospective studies strongly suggest that in going forward with prospective trials there is great promise that the molecular make-up of a given tumor will be directly correlated with whether a patient will respond or not respond to a given therapy.

One means of conducting retrospective studies is by use of clinical samples, which are of two major types: frozen samples and those that have been formalin fixed and paraffin embedded. There are, however, at least three major factors to take into consideration when completing a gene expression analysis of clinical samples. First, the use of frozen samples for microarray experiments requires a large amount of tissue and in the current experimental design and methods used by most investigators, a single microarray experiment will "use up" the entire biopsied material thus significantly restricting the use of the material for post-microarray validation experiments, other microarrays with different content, or other types of studies (such as proteomic analyses).

Second, microarray studies to date generally start with a homogenized biopsy and thus have to work with only samples that are highly enriched for tumor in order to minimize the amount of cellular heterogeneity within the sample. Unfortunately, this is not the "real world" situation in a clinical trial, where there is an inability to choose which subset of biopsies will be subsequently examined. The use of laser capture microdissection (Emmert-Buck et al., 3) obviates this issue by enabling the selection and capture of the desired cell type regardless of tumor load. "Real world" samples include those where the tumor load may be extremely low (i.e., 10%), and thus the sample may be heterogeneous with respect to total number of different cell types present in the biopsy, or the sample may contain a large amount of infiltrating inflammatory cells.

Finally, routine processing of samples in the clinical setting is significantly different from that conducted in a research laboratory. In particular, for routine analysis of biopsies from a clinical setting, the tissue is processed by formalin fixation and subsequently paraffin embedded. This process is a highly efficient method that is currently the standard in pathology suites. Unfortunately, only frozen samples are being currently utilized for microarray analyses because of the general technical inability of obtaining mRNA from formalin fixed samples for global mRNA expression analysis (i.e. for hybridization to cDNA or oligo microarrays). For example, Lewis et al. (5) expressly state that loss of poly A tails from mRNA is "the main cause of failure of the reverse transcription step".

Other attempts to utilize formalin-fixed tissue to produce cDNA for subsequent experiments have generated mixed results. For example, Karsten et al., (4) compared the use of frozen versus formalin-fixed tissues for use in cDNA microarrays via a tyramide signal amplification (TSA) system and concluded that " . . . formalin-derived RNA was not a good substrate for cDNA synthesis and clearly did not produce reliable hybridizations in our microarray experiments". On the other hand, Cohen et al. (9) describe the use of reverse transcription using random hexamers and real-time quantitative RT-PCR to amplify and thus detect expression of two chemokines. Similar use of reverse transcription PCR to amplify and detect expression of individual gene sequences was described by Lewis et al. (5), Lehmann et al. (6), Specht et al. (8), Masuda et al. (10), and Danenberg et al. (11). There has been no reported means to analyze gene expression at a cellular level by global amplification of extracted nucleic acids and subsequent analysis by multiplex analysis such as by use of a microarray.

Citation of documents herein is not intended as an admission that any is pertinent prior art. All statements as to the date or representation as to the contents of documents is based on the information available to the applicant and does not constitute any admission as to the correctness of the dates or contents of the documents.

DISCLOSURE OF THE INVENTION

The present invention provides a means to analyze the expression of various nucleic acid sequences in cells that have been fixed and optionally embedded. The act of fixation may be viewed as "freezing" the level of expression to that present in the cells at the time of fixation. The expression levels of various sequences, particularly as mRNA molecules in the cells, may thus be considered as having been frozen in time. A dynamic scene of cellular gene expression is thus captured as static molecules which represent the expression levels of various gene sequences in time. The invention provides a means of quantifying those expression levels, or viewing that scene, by the simultaneous generation of a plurality of cDNA molecules from the mRNA population of a cell. This "global" analysis of mRNA expression may be followed by subsequent transcription of said cDNA to produce RNA molecules for assay.

By rough analogy to a traditional photographic process, the expression level "scene" captured by fixation is used to generate cDNA "negatives" from which amplified RNA molecules may be produced for assay, such as one based on an array (or array-able) format such as a microarray. The array, which can contain a plurality of sequences capable of hybridizing to the amplified RNA molecules, is thus a "photograph" depicting gene expression in a cell.

The invention thus provides a means to "unlock" the gene expression data in a fixed and embedded tissue sample (or view the expression levels in the cells in such a sample) by the use of techniques to prepare and analyze the levels of messenger RNA molecules in said cells. In preferred embodiments, the invention is used quantitatively to determine the level of expression of one or more nucleic acid sequences. Alternatively, the invention may be used qualitatively.

Generally, a fixed cell containing tissue sample serves as the source of cell containing material for the practice of the invention. The sample is preferably sectioned and used for the extraction and preparation of RNA, optionally preceded by microdissection and/or removal of the embedding material. The extracted RNA is optionally heated to theoretically demodified and restore the RNA to a more native, pre-fixative, state. Polyadenylated RNA is then amplified by initially converting it, without selection, to cDNA via the use of an oligo dT primer which preferably is operatively linked to a promoter sequence that can direct transcription of the cDNA. The promoter may be a single stranded sequence (which is converted to a double stranded sequence upon synthesis of the second cDNA strand) or double stranded. This may be followed by transcription of the cDNA to produce amplified RNA having the same, or complementary sequence of the extracted RNA material. The amplified RNA is "global" because it is based upon polyadenylation rather than on selection of any particular gene sequence(s). Nevertheless, the RNA may be used to determine, or analyze for, sequences corresponding to the expression of nucleic acids in the cell, such as by hybridization to sequences on an array (or sortable array) format such as a microarray. Alternatively, the cDNA may be analyzed by other methods, including direct amplification (such as, but not limited to, PCR as discussed further below).

In an initial aspect, the invention provides an initial extraction and preparation of RNA from fixed cells method using a combination of proteinase treatment followed by RNA extraction and contact with a silica matrix. The extraction is preferably performed by use of a guanidinium containing compound or other means of producing the chaotropic effects of such compounds to denature proteins. This improves the condition of the RNA for subsequent analysis.

In a second aspect, the invention provides an improved method of preparing the RNA for reverse transcription by heating it. Without being bound by theory, this is believed to result in de-modification of RNA bases which were modified during fixation of the cells. This improves the condition of the RNA for subsequent uses.

In a third aspect, the invention provides an amplification method based upon amplifying RNA molecules containing poly A sequences at the 3' end. Such molecules have previously been determined to be degraded beyond the ability to serve as templates for reverse transcription (5). The amplification is made possible by initially reverse transcribing template polyadenylated RNA with an oligo dT primer, optionally comprising an operatively linked single or double stranded sequence of a promoter sequence. Reverse transcription of polyadenylated RNA in general permits the simultaneous production of a plurality of cDNA molecules which reflect the levels of the template polyadenylated RNA molecules of the cell. The invention may also be applied to the amplification of polyadenylated RNA molecules expressed by a pathogen as present in a fixed tissue sample.

In particularly preferred embodiments of the invention, all three of these aspects of the invention are combined for use together to produce information concerning gene expression in a fixed tissue sample.

The cDNA molecules may be used to transcribe RNA molecules containing the sequences of the template polyadenylated RNA or to transcribe RNA molecules complementary to such sequences. These transcribed molecules may be optionally labeled and used for hybridization to complementary sequences, such as those present on a microarray, to detect and optionally quantify, the expression of various sequences in the cell(s) from which the template polyadenylated RNA was isolated. Alternatively, the transcribed molecules are used to produce labeled cDNA molecules for hybridization to an array. The cDNA prepared from the template polyadenylated RNA, subsequent amplified mRNA, and optional subsequent cDNA, all optionally hybridized on a microarray, are products of the invention.

The cDNA molecules prepared from the template polyadenylated RNA may also be used in other methods of nucleic acid analysis. Non-limiting examples include PCR and quantitative or real time PCR amplification to determine, or analyze for, the expression levels of particular sequences via the use of specific primers. While the amplification may be performed in combination with hybridization to a microarray, this approach is not "global" because the PCR process requires the use of particular sequences in one or more primers which selectively amplify some sequences for analysis. These methods may be used to determine the expression levels of particular gene sequence(s) identified as correlated with an outcome as described below.

In another aspect, the invention is utilized in combination with fixed samples of tissue from subjects, preferably human, afflicted with, or suspected of having, a disease or other unwanted condition. Samples from subjects having the same disease or unwanted condition are preferably used in combination to identify the expression levels of gene sequence(s) as correlated with one or more aspects of the disease, or treatment or outcome thereof. Such samples have been collected over time and are often associated with detailed information on the disease, condition, treatment and/or outcomes of the subjects after the sample was taken. Non-limiting examples of such information includes that relating to the diagnosis, prognosis, treatment, response to treatment, and/or actual outcome(s) experienced by the subject over time after collection of the sample for fixation. In an alternative aspect, the expression levels of gene sequence(s) may be correlated with the condition of the subject prior to tissue sampling. Non-limiting examples include pre-existing diseases or unwanted conditions, age of disease onset, infection by infectious agents, exposure to mutagens or toxic agents, or genetic disorders. Such correlations are retrospective in nature, as opposed to correlations with outcomes that are to occur, which are prospective in nature. Furthermore, the expression levels of gene sequence(s) may be correlated with information on a disease, condition, treatment and/or outcome of the subject after the sample used to determine gene expression levels is obtained. The invention may thus be used to correlate gene expression with retrospective as well as prospective information from a subject from whom the sample was obtained. The correlations may be used to generate a model to assist clinical diagnostics by application of the correlations between gene expression level(s) and outcome(s).

In a further aspect, the invention provides for the compilation of the information concerning the expression levels of a plurality of nucleic acid sequences in the cell(s) of a fixed sample into a data structure. The data structure is optionally embedded in a solid medium or other article of manufacture, such as, but not limited to, a computer readable or other electronically readable medium. Preferably, the arrangement of the data structure permits the ready utilization of the information concerning expression levels to be used in methods of interpreting and utilizing expression level information in combination with an aspect of a disease, or treatment or outcome thereof. Correlations of gene expression levels with an aspect of a disease, or treatment or outcome thereof, may be stored as part of the same data structure or as a separate data structure.

The invention also provides for the ability to apply these correlations to gene expression information from a sample from another subject to identify said sample has having the same expression levels and the subject as likely to have the same aspect(s) of a disease, or susceptible to the same treatment or outcome thereof. Such samples from another subject include those that are not fixed, such as, but not limited to, a fresh or frozen sample. The expression level information from such other samples need not be obtained by the practice of the present invention, but rather may be by the use of other means, including, but not limited to, RT-PCR amplification of individual gene sequences and detecting expression of protein(s) encoding by the expressed sequence(s). Such methods of interpreting and utilization are optionally computer implemented.

The nucleic acid expression information in such a data structure preferably comprises information from one or more fixed tissue samples from six months to over 100 years ago and preferably comprises information concerning the post fixation treatments and/or outcomes of the subject from which the sample was taken. The information from a plurality of samples from a plurality of subjects may be correlated to identify specific expression levels of one or more gene sequences as relevant to an aspect of a disease or the post fixation treatments and/or outcomes of the subjects. This information may be applied in whole or in part to form all or part of a clinical definition or identification of a disease or unwanted condition in a subject. It can also be used to prognosticate as to the likely outcome experienced by other subjects with the same expression profiles in their tissue samples. The information may also be applied to use the expression level(s) of one or more sequences as defining a population or subpopulation of a larger group based upon diagnosis, prognosis, treatment, response to treatment, and/or actual outcome(s) correlated with the expression level(s). It may also be used to identify new aspects of a disease or treatment thereof based upon a relationship to the expression of one or more sequences.

In yet another aspect of the invention, methods of applying or interrogating this information to identify a cell containing sample from another subject as having the same expression level(s), and thus belonging to a population or subpopulation, are provided. The sample from another subject need not be fixed, but may be a fresh or frozen sample as non-limiting examples. These methods may be optionally computer implemented to maximize the beneficial application of the information that correlates expression level(s) to diagnosis, prognosis, treatment, response to treatment, and/or actual outcome(s). These methods would be advantageous in clinical applications of the invention to assist doctors and other medical personnel with the treatment and/or counseling of patients.

MODES OF CARRYING OUT THE INVENTION

Figure 1:
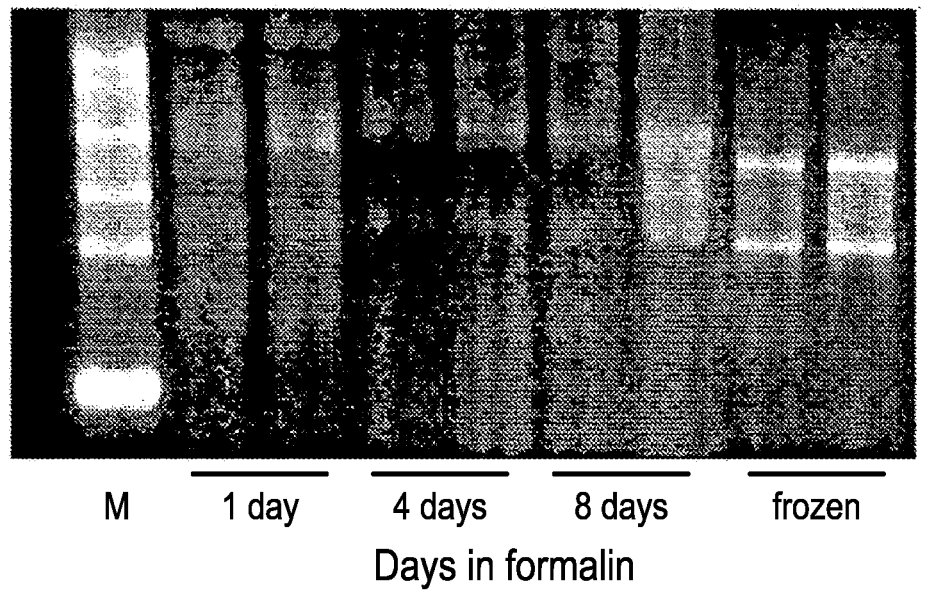
FIG. 1 shows RNA extracted from tissues fixed in formalin for 1 to 8 days.

The present invention provides for the global mRNA profiling of cells from (routine) clinical biopsies that are formalin-fixed (FF) and optionally paraffin-embedded (FFPE). Stated differently, the invention provides for the analysis of global mRNA expression in cell(s) of an FF sample. The invention may be applied to determine the expression of various genes within cells of a biopsy as well as serve as an indicator of protein expression within the cell.

In one embodiment, the invention optionally utilizes a microdissection technique to isolated cells from a formalin-fixed tissue sample followed by an RNA extraction protocol and subsequent amplification of mRNA to permit global mRNA expression profiling. The isolated cells are preferably those that appear to be non-normal. Normal cells may also be isolated and used as control cells. The identified expression profile may then be optionally used to identify gene sequences, the expression of which define a molecular expression signature for the cells and the condition which they are in. Such conditions include, but are not limited to, disease conditions, types, states, stages, and/or substages or subtypes. In preferred embodiments, the signature(s) (or expression levels) are used with historical data concerning the subjects from which the tissue samples were obtained to identify the cell(s), and thus a subject containing such cell(s), as sensitive or resistant to various treatment protocols. This information may then be used to direct treatment (to utilize the more effective treatment) in another subject, or a human patient, identified as having cell(s) with the same signature(s). In other embodiments, the expression levels are used with prospective data from the subject from which a sample was obtained.

In a particular exemplification of the invention, a process for obtaining gene expression data from FFPE samples is provided wherein the process comprises:

(1) Isolating a cell containing portion the FFPE sample, for example by microdissection (such as, but not limited to, laser microdissection), (2) Extracting the sample to collect an mRNA containing fraction, (3) Optionally purifying the mRNA, (4) Amplifying the mRNA, optionally using a method comprising:
   a. First strand DNA synthesis by reverse transcription with a primer containing both a poly (or oligo) dT region and a promoter portion,
   b. Second strand synthesis using exogenously supplied, random primers,
   c. In-vitro transcription (IVT) originating from the promoter present in said primer (optionally made double stranded via said second strand synthesis) to generate multiple copies of RNA molecules containing sequences complementary to the mRNA in the FFPE sample, and (5) Analysis of gene expression (as represented by mRNA levels) in the sample via hybridization of the IVT transcribed RNA to a microarray containing sequences of various gene sequences.

The invention may be practiced with samples fixed and embedded with a variety of methods known in the art. Briefly, such methods usually begin with cell containing tissue obtained from a patient afflicted with, or suspected of having, a disease or other unwanted condition. Non-limiting examples of tissue samples include a core biopsy, a removed tumor tissue, and a cytology sample. Other non-limiting examples include fine needle aspirates (FNA), needle biopsies, and ductal lavage samples. Non-limiting examples of tissue type include pancreas, large intestine, cancer of large intestine, muscle, urinary bladder, kidney, lung, brain, lymphoma, and any other tissue of a multicellular organism.

The sample is quickly immersed in a fixative means such as a solution with a protein crosslinking activity, such as but not limited to a formaldehyde solution, glutaraldehyde solution, formaldehyde-alcohol mixed solution, alcohol solution, Bouin's solution, Zenker solution, Hely solution, osmic acid solution, Carnoy solution, and equivalents thereof. Non-limiting examples of fixative alcohols include ethanol and isopropanol. This is preferably done as quickly as possible to minimize cellular changes that may occur after collection and before fixation. It also maintains the fine structure of the tissue and cells therein.

The fixative preferably contains formaldehyde or paraformaldehyde or other means of fixing tissue samples. Preferred fixatives include buffered formaldehyde, such as phosphate-buffered formaldehyde solutions, or other means of buffering formaldehyde or paraformaldehyde. The fixed samples may be maintained as "wet samples" considered as part of a "wet archive" or are optionally treated with an embedding means such as paraffin or other wax like hydrocarbons. While other fixatives such as acetone, Clark's, Carnoy's, glutaraldehyde, mercuric chloride containing formaldehyde formulations, and Bouin's fixative may be used, the invention is preferably practiced with the large number of archival tissue samples that are formalin fixed and paraffin embedded (FFPE). The fixatives may optionally contain magnesium cations.

The time of fixation is preferably from 16 to 48 or 72 hours at temperatures from about 4° C. to room temperature. Times of about 16, about 20, about 24, about 28, about 32, about 36, about 40, about 44, about 48, about 52, about 56, about 60, about 64, about 68 and about 72 hours may be used in the practice of the invention. Alternatively, shorter times of about 3, about 4, about 5, about 7, about 8, about 9, about 10, about 12, about 14, and about 15 hours may also be used. Such shorter periods may be more appropriate for smaller samples, such as in the case of FNA or needle biopsy samples. Temperatures of about 4, about 8, about 12, about 16, about 20, about 24 and about 26° C. may be used. The invention may also be practiced with a sample fixed for other times, such as for 4, 5, 6, 7, or 8 days and at other temperatures than those disclosed herein. After fixation, the samples may be embedded in paraffin using standard techniques and means for embedding followed by storage under art utilized conditions, such as at temperatures from about 4° C. to room temperature.

The age of the fixed and embedded samples are preferably from about 6 months to about 100 years old for the practice of the invention to correlate expression levels with actual outcomes of the patient from which the samples were taken. Obviously, samples less than about 6 months of age may also be used in the practice of the invention, but it may not be possible to correlate the expression levels in such samples with actual outcomes of the patient from which they were obtained due to the short time interval. The expression levels of samples without associated outcome information may nonetheless be used in comparison to the expression levels and correlated outcomes generated by the use of the invention with older samples.

Preferred older samples for correlation of expression levels to actual outcomes are about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 25 years, about 30 years, about 40 years, about 50 years, about 60 years, about 70 years, about 75 years, about 80 years, about 90 years, or about 100 years old.

A section of a fixed sample is preferably used in the present invention to preserve material of the fixed sample for subsequent uses. Sectioning may also be used in combination with the optional use of microdissection as discussed below. Preparation of sections may be by any techniques and means for sectioning. In one embodiment, the paraffin blocks are sliced into sections by the use of a microtome. Preferably, the microtome has been carefully cleaned to remove or reduce the likelihood of contamination by extraneous nucleic acid molecules or nucleic acid degrading agents. A non-limiting example includes the use of a nonhazardous zylol substitute along with the use of a 3% hypochlorite solution for the treatment of plastic ware used in combination with the sectioning process.

Sections are optionally, but preferably, deparaffinized by procedures known in the art to remove the bulk of paraffin from a sample. Various techniques for deparaffinization are known and any suitable technique may be used in practicing the present invention. Such methods include, but are not limited to, washing with an organic solvent or agent to dissolve the paraffin. Non-limiting examples of suitable solvents include benzene, toluene, ethylbenzene, xylenes, D-limonene, octane, and mixtures thereof. These solvents are preferably of high purity, usually greater than 99%.

Paraffin is removed by washing with an organic solvent or agent followed by its removal. The volume of organic solvent used and the number of washes necessary will depend on the size of the sample and the amount of paraffin to be removed. A sample may be washed between 1 and about 10 times, or between about two and about four times. A typical volume of organic solvent is about 500 µL for a 10 µm tissue sample. Other methods for deparaffinization may also be used.

After deparaffinization, samples are preferably rehydrated, such as by step-wise washing with aqueous lower alcoholic solutions of decreasing concentration. Ethanol is a preferred lower alcohol for rehydration while other alcohols may also be used. Non-limiting examples include methanol, isopropanol and other C1-05 alcohols. The sample is alternatively vigorously mixed with alcoholic solutions followed by its removal. In one embodiment, the concentration of alcohol is stepwise lowered from about 100% to about 70% in water over about 3 to 5 steps with an about 10% or less decrease in each step, such as via 100%, 95%, 90%, 80%, 70% steps. Deparaffinization and rehydration may also be conducted using other reagents known in the art.

With or without deparaffinization, the sections are optionally stained to visualize cells within the sections, preferably by use of means that do not cause the loss of RNA. Staining with hematoxylin and eosin (H&E) may be in some embodiments of the invention, especially where there is subsequent use of the optional microdissection step to isolate one or more individual cells. Staining also permits the evaluation of the sections to determine whether subsequent microdissection is necessary based upon the presence or absence of contaminating cells which are preferably not used for the extraction of RNA. The presence of excess infiltrating immune cells in a sample of cancer cells where gene expression in the cancer cells is of greatest interest is a non-limiting example of a situation where microdissection to isolate the cancer cells for use is desirable.

Microdissection of a tissue section may be performed by any means suitable therefor. Non-limiting examples include laser capture microdissection (LCM) or laser microdissection (LMD). The isolation of cells advantageously permits the exclusion of unrelated cell types such as, but not limited to, infiltrating immune cells, as well as exclusion of cells of other origins and/or phenotype(s). Microdissection may be advantageously used in the practice of the invention because contaminating, non-disease related cells (such as infiltrating lymphocytes or other immune system cells) may be eliminated from a fixed and embedded tissue sample or -section to avoid affecting the determination of gene expression in the cells of interest. A non-limiting example of such contamination is present where a biopsy is fixed and then used to prepare the section. The capture of about 100-1000 or more cells is preferred for the practice of the invention, however, the use of fewer cells is also possible.

Microdissected samples that have not been deparaffinized may optionally undergo paraffin removal by use of the methods described above.

As noted herein, sectioning and microdissection are both optional steps before the extraction of RNA from cells as utilized in the present invention. The invention may be practiced with a variety of extraction protocols, including acid guanidinium thiocyanate/phenol-chloroform, proteinase K digestion at various temperatures and for various times, oligo dT based chromatography, and a guanidinium thiocyanate lysis followed by binding to glass beads or another silica based matrix (see references 13-15). The present invention also provides, however, a new method of RNA extraction as described below. This method has been unexpectedly found to provide an enhancement in the amount and quantity of RNA extracted from a fixed sample.

The invention also provides for an optional heating step believed to de-modify nucleic acid bases that are often modified due to fixation with formaldehyde. The invention is not, however, to be bound by this theory, which is provided to assist with the understanding of the invention and not as a limitation thereof. The theoretical modifications are the addition of mono-methylol (—$CH_2OH$) groups at various rates. The modified bases have altered basepairing capabilities and so can have deleterious effects on any aspect of the invention wherein RNA molecules in the sample are to be hybridized to other nucleic acids, such as during priming and nucleic acid polymerization events such as reverse transcription.

In particular, the present invention provides for the use of a longer heating period without deleterious degradation of RNA molecules. Preferably, the heating is at 70 or about 70° C. for a period of at least one hour, preferably greater than 60 minutes, such as 120 or 180 minutes although periods up to 8 hours may also be used. The heating period may thus be from greater than 60 to about 75, about 90, about 105, about 120, about 135, about 150, about 165, about 180 minutes, about 4 hours, about 5 hours, about 6 hours, about 7 hours, or about 8 hours. Most preferred is the use of heat for about 3 hours, such as from 150 to 210 or 165 to 195 minutes. And may be performed in a variety of buffered solutions, such as, but not limited to, 10 mM Tris-HCl at pH 8.0 or thereabouts. Equivalent acetate buffers may also be used. The ability to utilize such conditions is an unexpected discovery in light of evidence that RNA degradation and decreased yields occur upon 60 minutes of heating at 70° C. (see Masuda et al. (6)).

The invention provides a means to globally amplify polyadenylated RNA from the cell(s) of a fixed sample by use of a poly or oligo dT primer. The primer is used to hybridize to the poly A tails of mRNA molecules for the synthesis of a first cDNA strand. Such strands may be relatively short, on the order of about 100-400 basepairs or may be longer, such as up to 1-6 kilobase. This reflects a surprising result based upon the understanding in the art that the poly A tails of mRNA extracted from fixed samples were too degraded to permit reverse transcription via a poly or oligo dT primer (see Lewis et al. (5)). A variety of dT based priming methods may be used in the present invention, and non-limiting examples include those described in U.S. Pat. Nos. 5,545,522, 5,716,785 and 5,891,636, where synthesis of a second cDNA strand is performed without exogenous primers. A preferred method is described in published International Application WO 02/052031 (corresponding to PCT/US01/50340 filed Dec. 21, 2001) and utilizes random primers for the synthesis of the second cDNA strand.

The cDNA may be used for direct analysis of gene expression, such as, but not limited to, being hybridized to labeled polynucleotide probes or being labeled for detection followed by hybridization to probes. Or the cDNA may be analyzed indirectly after amplification by a PCR technique followed by detection. Alternatively, the cDNA may be used for in vitro transcription (IVT) in the manner described in International Application WO 02/052031. Briefly, the first strand cDNA comprises a single stranded or double stranded form of a promoter sequence introduced via an operative linkage to the poly or oligo dT primer used to synthesize the first cDNA strand. The resultant double stranded cDNA may be transcribed by initiation from said promoter to produce mRNA transcripts. These transcripts would contain sequences complementary to that of the polyadenylated RNA used to generate the cDNA. A primer linked promoter of the invention is preferably a T7 promoter, but other non-limiting examples include the T3 and SP6 promoters.

In another alternative IVT embodiment, the promoter sequence may be introduced via an operative linkage to the random primers used to synthesize the second cDNA strand. The resultant double stranded cDNA may be transcribed by initiation from said promoter to produce mRNA transcripts containing sequences of the polyadenylated RNA used to generate the cDNA. In either of the above IVT embodiments, the transcribed (or amplified) RNA may be analyzed directly by hybridization to labeled polynucleotide probes or labeled for detection followed by hybridization to probes. The transcribed RNA may also be analyzed indirectly after amplification by a PCR technique or by conversion to cDNA which is analyzed as described above. Both of these latter techniques can of course rely upon the use of primers that are complementary to sequences at the ends of the cDNA.

In a particularly preferred embodiment, a portion of the amplified RNA is used to produce labeled cDNA conjugated to a fluorescent dye, such as by use of labeled nucleotides. A second, and compatible, fluorescent dye is used to label a reference amplified RNA. Equal amounts of both labeled cDNAs are hybridized to a microarray of various nucleic acid sequences individually located at discrete locations of the microarray. After hybridization and washes, the microarrays are scanned and quantitated for hybridization signal intensity to each sequence on the microarray. The fluorescent intensities, after normalization, can be expressed as ratios of each amplified RNA to the reference amplified RNA to represent gene expression levels of the sequences of each amplified RNA. Alternatively, the amplified RNA is labeled as it is produced. The labeled amplified RNA is optionally fragmented and hybridized to probes, such as, but not limited to, those immobilized on a microarray. The RNA may be labeled directly for detection, such as by fluorescently or radioactively labeled nucleotides, or labeled indirectly, such as by biotinylated nucleotides which are detected with a fluorescently or radioactively labeled streptavidin. Therefore, both DNA and RNA molecules corresponding to the amplified RNA of the invention may be used as probes. Another form of indirect labeling is by use of allylamine to conjugate a label, such as a fluorescent dye, to a nucleic acid molecule (see Example 1 below for an exemplification).

Preferably, the sequences on the microarrays are those of the 3' portions of various gene sequences expressed in a cell of an FFPE sample as analyzed by use of the present invention. As recognized by the skilled person, the 3' portion is closest to the site of polyadenylation and thus most likely to be reverse transcribed, and thus found in the resulting cDNA, in the practice of the present invention.

Information on the expression levels of various sequences, such as, but not limited to, the ratios of fluorescent intensities as described above, may be stored via an appropriate means as preferred by the skilled person. In preferred embodiments of the invention, the information is stored magnetically or electronically, and more preferably in a form that is computer readable. The expression level data may be stored as raw data or as processed data (such as, but not limited to, normalized, corrected, or in the form of ratios) or as combinations thereof. Preferably, the processed data is in the form of raw expression levels that has been converted into an expression value or expression index for each gene sequence from a sample. In preferred embodiments, the information is stored as a data set and/or a data structure. One non-limiting example is storage as a table with stored records. A tabular storage means may be viewed as data fields which store information like a subject identifier (with or without information on expression levels of various sequences from a subject's FF or FFPE sample) and/or a gene sequence identifier. These identifiers may also serve as descriptive names for the respective fields. Preferably, both the subject identifier and the gene sequence identifier fields are designated as primary "keys" used to uniquely identify a record. A tabular information storage means of the invention is preferably specific for a disease or unwanted condition and may be stored on a computer-readable medium. They may also be a data structure to support specific manipulation, "look up", or application functions as provided by the instant invention.

In a particularly preferred embodiment of the invention, the gene expression level information is combined with other information about the donor from whom the FF or FFPE sample was obtained. Preferably, the subject is a human patient, and such other information includes, but is not limited to, that which is normally obtained in relation to medical or clinical treatment. Non-limiting examples include age, weight, height, medical history as well as health status and/or symptoms or disease type or status at the time the sample was obtained. A further example is information obtained from a pathologist's review of the sample. The latter items are of relevance with respect to patients that are afflicted with, or suspected of being afflicted with, a disease or other unwanted condition. This additional information may also be stored using a tabular storage means as described above or in a separate storage means.

When available, the other information may also include information concerning the patient's diagnosis and care following the isolation of the sample. Generally, such information is that which is normally maintained in a patient's medical history over time to record treatments and outcomes (including further development, eradication, or remissions of a disease) as well as a medical practitioner's notes and/or observations. Non-limiting examples of the latter include cases of unusual genetic makeup of the patient, difficulties in determining a clear diagnosis or course of treatment, and/or unusual disease progression in spite of treatment. Other non-limiting examples of such additional information include that relating to the diagnosis and/or prognosis of the patient, the treatment(s) applied, the responsiveness of the patient and disease to said treatment(s), the presence or absence of side effects from said treatment(s), the cause and age of death of the subject, and other outcome(s) for said patient and disease. In particularly preferred embodiments of the invention, information regarding the treatment(s) applied and the outcome(s) is combined with information concerning gene expression levels.

Preferred information relating to outcomes) is that which is collected over time, including, but not limited to, information concerning the further progression, eradication, or remission of the disease, the success or failure of the treatment(s), and life span of the patient following treatment. This additional information may also be stored using a tabular storage means as described above or in a separate storage means. Alternatively, it may be combined with a tabular storage means as described above by introduction into a receiver object that is used in combination with the tabular storage means. This combination is preferably stored in the same medium.

Other information that may be correlated with the expression levels of gene sequence(s) include that of the subject at the time of tissue sampling. Non-limiting examples include pre-existing diseases such as autoimmune disease, unwanted conditions such as excess inflammation, and infection by a bacterial, viral, or fungal agent. Additionally, the same type of information collected about the subject after isolation of the sample may be correlated. Such data is prospective in nature, and includes that from a clinical trial as a non-limiting example. The invention may thus be practiced with the use of data that is retrospective and prospective relative to the time of FF or FFPE sample isolation. Additionally, the invention may be practiced with data that is retrospective and prospective relative to the time of RNA extraction and cDNA preparation.

The ability to determine the expression levels of various gene sequences in an FF or FFPE sample provides a unique means to relate the expression levels to information concerning disease or patient outcome(s) over time because the FF or FFPE sample can serve as a point in time reference from which to correlate the outcome(s). FF or FFPE samples that are sufficiently old to be combined with data concerning disease or patient outcome(s) over time, are thus an archive which can be tapped to correlate gene expression with disease progression and outcome.

The invention "unlocks" the archive by providing access to the global gene expression data stored therein in contrast to other individual bits of expression data based upon analyses of individual gene sequences. The ability to simultaneously evaluate a plurality of gene sequence expression levels in a single sample allows for the data concerning these levels to be compiled into a data structure for subsequent use, analysis and manipulation.

Generally, means for the compilation of data are known in the art, but the invention provides means for the combination of the gene expression data from FF or FFPE samples with additional information concerning a subject or patient as described herein. The means and resulting combinations provided by the instant invention provide in part the ability to generate molecular models for disease as well as predictive models to assist in diagnosis and treatment of disease. The generation and use of this combined data are described further below.

Methods of applying or interrogating the "profile" of gene expression level(s) correlated with an outcome include the diagnosis of a subject suspected of having a disease in whole or in part by comparison of gene expression in a sample obtained from the subject to one or more profiles generated by the present invention. The same or similar gene expression profiles indicate the presence of the same disease. The profile may thus be viewed as part of a definition of a disease or as a tool for differential diagnosis to exclude other diseases or unwanted conditions from the diagnosis. The profile may also be considered as defining one or more characteristics of a subject with the same or similar cellular gene expression profile. These characteristics include the various outcomes as described herein as well as characteristics that have yet to be recognized.

The profile may also be used in methods of determining treatment for a subject by using the diagnosis obtained as described above to determine treatment. Alternatively, the profile may include an indication of an efficacious treatment based upon the treatment outcomes of subjects whose samples were used to generate the profile. The same or similar profile of gene expression level(s) in a sample from a subject seeking or in need of treatment would indicate use of the treatment found to be efficacious for the subjects whose samples were used to generate the profile.

Profiles of the invention may also be used to provide information concerning prognosis or counseling to a subject afflicted with a disease. Information on disease outcomes that have been associated with gene expression level(s) of the invention may be provided to subjects whose tissue samples have been found to have the same or similar gene expression level(s).

RNA Extraction

RNA may be extracted from cells of an FFPE sample via protocols using acid guanidinium thiocyanate/phenol-chloroform, proteinase K digestion, oligo dT based chromatography, and a guanidinium thiocyanate lysis followed by binding to a silica based medium. The use of proteinase K digestion is normally followed by an extraction step using phenol or phenol-chloroform to remove the degraded proteinaceous material as well as the proteinase K protein for isolation of the RNA. As obvious to those skilled in the art, proteinaceous material is separated, via the presence of the non-aqueous phenolic phase, from nucleic acids, including the RNA, which remains in the aqueous phase.

The present invention provides an improved method of RNA extraction comprising the use of proteinase K followed by denaturation with a guanidinium containing compound as a chaotropic agent to denature the contaminating proteinaceous material. The RNA is then isolated by binding to a silica based matrix which does not bind the contaminating proteinaceous material. This is based in part on the unexpected discovery that a guanidinium containing compound is capable of denaturing proteinase K and allowing purification of RNA away from it. The bound RNA may then be eluted from the silica based matrix using conventional means for subsequent manipulations.

Non-limiting examples of guanidinium containing compounds include guanidinium isothiocyanate (GITC or guanidinium thiocyanate, GSCN) and guanidinium hydrochloride. They may be used with a variety of anionic counterions from which appropriate ones may be selected by the skilled practitioner. The guanidinium solution used in the invention generally has a concentration in the range of about 1 to about 5M with a preferred value of about 4M and is preferably buffered to a pH of about 3 to about 6, more preferably about 4, with a suitable biochemical buffer such as Tris-HCl. The guanidinium containing solution may optionally contain one or more RNAse inhibitors.

Other chaotropic agents with the activity of guanidinium containing compounds may also be used as long as an effective concentration RNA is purified from an FFPE sample in an amount equivalent to that using a guanidinium containing compound. Non-limiting examples of such agents include urea, formamide, potassium iodide, potassium thiocyanate and equivalents thereof.

The proteinase K treatment is preferably performed at a temperature of 42° C. or thereabouts to 60° C. for at least 8 hours, preferably at least 16 hours, and more preferably at least 24 hours. Other conditions may be any that are suitable for RNA extraction. A non-limiting example is 10 mM Tris-HCl at pH 8.0 or thereabouts, 2% SDS, and from 100-500 μg/ml proteinase K.

The above refers to embodiments of the invention where fixed cells of a sample are be treated with proteinase K to prepare a cell lysate from which proteinaceous material is removed before further preparative actions on the nucleic acid material. A non-limiting example of a proteinaceous material removal step beyond the use of phenol or GITC described above is the use of an aqueous solution of anionic, polyelectrolyte material that bind proteinaceous material and/or divalent cations. Such material may be particulate in nature and/or applied as a slurry, such as available from Ambion. Following removal of the proteinaceous material, the sample is optionally DNased and then used for RNA amplification. If the optional DNase is used, a proteinaceous material removal and/or denaturation step can be used before the steps for RNA amplification.

Generation and Use of Gene Expression Level Data

Data of the gene expression level data from an FF or FFPE sample obtained by the practice of the methods of the present invention are preferably organized into one or more data fields of a computer readable medium comprising a plurality of data fields. Preferably, the data is in the form of expression values or indices that may be correlated with other data from the sample donor. The data fields may be optionally organized as one or more datasets and/or one or more data structures. A data field is stored in a range of addresses in said computer readable medium and may be treated as representing gene expression level data from an FFPE sample.

Generation of gene expression data is preferably by use of hybridization to an array, such as a microarray as described herein. Nucleic acid probes containing various gene sequences are individually located at defined positions of a microarray. The probes are preferably immobilized on the microarray and represent different genes or gene fragments, optionally having a commonality. Non-limiting examples of commonalities include expectation that they may be expressed in a given cell type, tissue, or organ; expression in a disease state or unwanted condition; similar biological function(s); or are all the expressed genes for a given organism. Alternatively the invention may be practiced with the use of materials that are capable of being sorted into an array, such as that available from Illumina.

Various technologies are known for the manufacture of microarrays, and they may be composed of probes located at a variety of densities. Non-limiting examples include from about 10 to about 500,000 probes (and thus gene sequences) in a square centimeter. The probes of such microarrays are hybridized to labeled nucleic acid molecules derived from an FF or FFPE sample as described herein. The observed intensities of the hybridization to individual probes reflect expression levels or data of individual sequences in the FF or FFPE sample.

There are generally control samples, derived from mRNA of a known source and/or quantity, and test samples, derived from mRNA from an FF or FFPE sample as described herein. One non-limiting example of a control sample are normal cells, preferably from the same FF or FFPE sample used for the test sample, which would contain non-normal cells. Normal and non-normal cells can be isolated by use of microdissection as described herein and generally used in the art.

The control and/or test sample is used in combination with a reference mRNA, such as that which acts as a control between microarray experiments, with one or more non-zero signals for expression of various sequences. Non-limiting examples include the human, rat, and mouse Universal Reference RNA from Stratagene. The test samples may be that from an FF or FFPE sample of a subject suffering from a disease or which has been treated with a drug or other agent. The samples may also be those from tumors that respond to a particular treatment or drug regimen and those that do not respond. Gene expression levels in such differential samples may also be evaluated against each other and against control(s) to identify gene expression levels that are correlated with one sample and not the other.

Preferably, the hybridization of various samples is conducted under the same conditions, and in particularly preferred embodiments, the control and test samples are labeled differently and hybridized to the same microarray. Preferred labels are fluorescent, such as, but not limited to red and green (e.g. Cy5 and Cy3) mono-reactive dyes from Amersham, used to directly or indirectly label nucleic acid molecules. The data from each hybridization, whether as raw hybridization signal intensities or after manipulations such as, but not limited to, spot filtering, background correction, and/or normalization, may be stored in a computer readable medium as described herein. Preferably, the data is stored as normalized ratios of test sample intensities to control sample (reference RNA) intensities although other forms of processed data, include that which adjusts for statistical variables in the samples and raw expression level data, to produce an expression value or index may also be used. The data is preferably loaded into data fields to facilitate the analysis of the results in comparison to other information concerning the subject from which the FFPE sample was obtained. Other data, such as that on each sample, hybridization conditions, and microarray information, are optionally stored with the above data.

The hybridization signal intensities are preferably measured by a microarray reader/analyzer. This is generally conducted with various known hardware and software components for use with hybridization experiments and the microarray reader/analyzer outputs raw or processed expression data for each site or element of a microarray. The data may include fluorescence intensity values for each element on the microarray. The processed data permits a determination of expression or non-expression of individual gene sequences, optionally as a ratio relative to a control. Optionally, the level of any expression can be based on hybridization data from multiple sites having the same or different probes for given gene sequence, such as multiple probes for a given gene sequence. The processed levels may be averaged before use.

Gene expression data may be stored in the same or a different file with other data, such as, but not limited to, the locations and identities of gene sequences represented on the microarray, FF or FFPE donor information, microarray design information, biological information, data source, FF or FFPE sample information, descriptions of the experimental samples and additional experimental data, and hybridization information.

The information on gene expression, represented as hybridization signal intensities (raw data), or expression indices (such as ratios of raw intensities), are "expression data" and reflects the expression of various gene sequences within an FF or FFPE sample. The expression data may optionally include a message and/or a series of prompts to prompt the entry of additional information related to the expression data, the FF or FFPE sample from which the data was obtained, or the subject from which the sample was obtained. Non-limiting examples include outcome data from the subject from which the sample was obtained, such as diagnosis, prognosis, treatment, response to treatment, and/or actual outcome(s) experienced by the subject over time. The expression data and the prompts may be in the form of data fields stored in a range of addresses of a computer readable medium.

A computer readable medium comprising the expression data may optionally further comprise an "outcome data" object which serves as a central unit of information that contains not only the expression data, but also receives outcome data of the subject(s) from which the FF or FFPE sample, and thus expression data, was obtained. The outcome data may also be considered the phenotypic data from the sample donor, which includes donor age, demographics, and history; disease history; diagnosis history; treatments applied and responsiveness thereto; mortality; recurrence of disease, including changes in the form of the disease upon recurrence; and other information as described above. The outcome data object may be stored in a range of addresses separate from the expression data or in a range of addresses that also stores a data field representing expression data. When the outcome data object is created, it has locations set aside to store phenotypic information of the outcome(s) experienced by the subject(s). This is a different approach from databases that only store outcome information because the outcome object also contains the expression data. This provides an advantage not previously available because the outcome object can be used to correlate the expression data with the phenotypic data/outcome(s) to identify the expression of particular gene sequences as linked with one or more phenotypic outcome(s).

It also permits the object to be passed from one location or source to another while containing all information relating to one or more outcomes. These benefits permits greater ease and speed of use while minimizing the likelihood of lost information.

After creation of the outcome data object, it is ready to receive various phenotypic and outcome information or data from a user or other source. In a preferred embodiment, outcome data is introduced electronically. The expression data of an outcome data object may be updated at anytime. Such an update will necessarily generate an updated outcome data object, optionally capable of receiving outcome data from the source corresponding to the source of the updating expression data. Such updated expression data may supersede and replace previous expression data.

A user may input outcome data into an outcome data object in response to a prompt for outcome information, which may be displayed from the expression data. The outcome information is stored in a data field of the outcome data object adapted to receive and store outcome data, which may be textual or numerical in form. The outcome data object also optionally permits a user to enter additional information not limited to outcome information.

After receipt of outcome data, the expression data and outcome data may be used to correlate the expression of one or more gene sequences as associated with one or more outcomes. Stated differently, the expression data (such as expression indices for various gene sequences) is associated with phenotypic data to identify various indices and gene sequences as correlated with outcome(s). The expression indices may be arranged in a data matrix such as a table showing individual indices for individual gene sequences of individual FF or FFPE samples. The identifiers of the individual samples are then used to associate phenotypic data from the donors of the samples with the expression indices. This association process may also be described as constructing a model or expression profile to explain correlations between expression indices and phenotypic data for individual samples. Two general modeling methods that may be used in this aspect of the invention are statistical models and those based upon artificial intelligence. Non-limiting examples of the former include logistic regression and classification trees. These may be used to predict whether a particular expression index is predictive of a phenotypic outcome. A non-limiting example of the latter is a neural network.

Model building may be viewed as supervised learning based upon the expression indices and phenotypic data, which may be used as a training set upon which a model or profile is constructed. The resultant model or profile is preferably built to minimize error rates, such as by increasing the confidence/probability/likelihood level at which an expression index would be identified as predictive. This may also be referred to optimization of the model or profile, which may also result in the reduction in the actual number of expression indices included as predictive of an outcome. The invention provides for the ability to construct multiple models or profiles from the same expression data and phenotypic data, all of which may be optimized before being compared and subject to selection for possible use.

Model construction and selection are preferably conducted with the application of domain knowledge to include or exclude data based upon recognition of their relevance or importance to the model or profile being sought. As a non-limiting example, the recognition that gene sequence "A" express a protein product "A prime" which in turn controls expression of expression of gene sequence "B" is relevant to model construction to potentially adjust the model to account treat increases or decreases of "B" expression as corresponding to similar increases or decreases in "A" expression rather than as an independent index that can be correlated to phenotypic data. Domain knowledge also refers to the recognition of the significance of data analysis techniques as preferred for use in model construction. As a non-limiting example, the use of Pearson's correlation (Pearson Product Moment Correlation) to relate gene expression indices with phenotypic data as a linear relationship in many cases.

A model or profile after selection can be validated by use of additional expression data and phenotypic data of an FF or FFPE sample. As a non-limiting example, if a model is constructed and selected wherein a decrease in expression of gene sequence "X" is correlated with patient mortality within 24 months, then the model can be validated based upon its ability to predict the phenotypic outcome of mortality within 24 months of a sample donor if the sample has the same decrease in gene sequence "X" expression. Once validated, the model or profile may be considered predictive for various phenotypic outcome(s) based upon particular gene expression indices. Of course the model may be refined or altered by use of a different training set or additional data introduced into an existing training set or different selection criteria or application of different domain knowledge and then re-validated. Models produced by the present invention preferably are those where the expression level of a single gene sequence, or 2-5 or 5-10 gene sequences is predictive of a phenotypic outcome, although the use of 10-20, 20-30, 30-40, 40-50 or more than 50 gene sequences may also be used in a model.

In preferred embodiments of the invention, the expression data comprises gene expression information from multiple FF or FFPE samples from subjects with the same disease, unwanted condition, or biological status. The phenotypic or outcome data is preferably information on one or more outcomes from the donor of the FF or FFPE samples used to produce the expression data.

By way of example offered to improve the understanding of the invention and not intended to limit the scope of the invention, an outcome to be correlated with expression data may be responsiveness of a cancer to a particular treatment regimen, such as breast cancer to tamoxifen. The outcome may be disease status (afflicted or disease free) at various times after start of tamoxifen treatment. This outcome data may be used to correlate one or more gene sequences the (increased or decreased) expression levels of which is associated with either success or failure of tamoxifen treatment at various times after start of treatment. The correlation may also be used to identify one or more gene sequences the (increased or decreased) expression levels of which defines a population of subjects having such expression levels and as benefiting or not benefiting from treatment with tamoxifen. The populations may also be viewed as those with breast cancer that is sensitive or resistant to tamoxifen.

The correlation may also be used to identify subpopulations such as subjects with gene sequence levels which are associated with long term or short term success with tamoxifen treatment. These subpopulations may also be viewed as those subjects with various expected (or projected) survival times.

Another non-limiting example is the use of training data set from FFPE specimens (excision biopsies) from women >50 yrs. old who are ER(+), node (−), and tumors less than 2 cm (at the greatest dimension). Preferably, at least 10 samples from women of each group are used; more preferred is the use of at least 15, at least 20, at least 25, or at least 50 samples from each group. The women will have undergone surgery and been given tamoxifen for five years. A subset of these women will have had recurrence of disease and a subset will not. Model building (gene expression profiling) on the subset of women whose disease recurred in comparison to those without recurrence permits the identification of gene sequence(s) the expression of which are predictive of breast cancer recurrence or non-recurrence in such a patient population. The patients in whom recurrence occurred or did not occur are subpopulations as provided by the instant invention.

As would be obvious to the skilled practitioner, the above examples are exemplary in nature and the responsiveness to other drugs or treatment regimens, including but not limited to radiation therapy or combination radiation and chemotherapy, may be the focus in applications of the instant invention. Additionally, this aspect of the invention is not limited to analyses with therapeutic outcomes. For example, correlations with life expectancies or the occurrence of metastases may also be practiced by use of the instant invention.

The outcome data object thus provides a single contained unit of information for the analysis and comparison of expression data and outcome data. An analogy to the object is a folder or file where all information for a correlation of outcome to expression can be placed. The file can then be carried from one individual or location to another for analysis of the data therein or the introduction of additional expression and/or outcome data. Because expression level data is generated from unselected polyadenylated mRNA levels in FF or FFPE samples as provided by the present invention, the expression data is more complete and thus permits more comprehensive identification of gene sequence expression level(s) as correlated with outcome(s).

Using an outcome data object also opens up a wide variety of options. As noted above, the object can be used to correlate gene expression levels and one or more outcomes to define a gene "expression profile" comprising gene expression levels that are associated with said outcome(s). The "expression profile data" represents the range of expression level(s), optionally in the form of hybridization signal intensities or ratios thereof or other expression indices, that are associated with an outcome. The expression profile data may optionally include a message and/or a series of prompts to prompt the entry of additional information, such as the expression levels of a sample for comparison to the expression profile, which would be used as a predictive model. The expression profile data and the prompts may be in the form of data fields stored in a range of addresses of a computer readable medium. This medium may be the same or different from that comprising a expression data and an outcome data object.

The present invention also provides a computer readable medium comprising the expression profile data, which may optionally further comprise a "profile data" object. The profile data object serves as a central unit of information that contains not only the expression profile data, but also receives expression data from a test sample. The test sample may be an FFPE sample with a known outcome to test the ability of the expression profile data to identify the outcome for validation purposes. Alternatively, the test sample may be a fresh, frozen, or recent FF or FFPE tissue sample from a subject afflicted with a disease or seeking treatment to predict the subject's outcome, or provide information on the efficacy of various treatments, by comparison to the expression profile data.

As a non-limiting example, the present invention provides a means to identify gene expression profiles associated with various stages of breast cancer, such as atypical ductal hyperplasia (ADH), ductal carcinoma in situ (DCIS), and invasive ductal carcinoma (IDC). The expression profile data associated with each of these stages may be part of a breast cancer profile data object which is able to receive expression data from a test sample of a patient who has, or is suspected of having, breast cancer. A comparison of gene expression level(s) of the test sample and the profiles permits the determination that the patient has none, one, or a combination of the above described stages of breast cancer. The expression data on the test sample may generated by the use of (global) polyadenylated mRNA amplification as described herein or by the use of PCR based amplification of gene sequences the expression of which are relevant to the breast cancer expression profiles. The use of global mRNA amplification permits the resulting expression data of a test sample to be compared and analyzed with other expression profiles.

The profile data object may be stored in a range of addresses separate from the expression profile data or in a range of addresses that also stores a data field representing expression profile data. When the profile data object is created, it has locations set aside to store expression level data from one or more test samples. The expression level data is preferably received into one or more data fields of the object that have been adapted for such receipt and for ready comparison to the expression profile data. This provides the ability to predict outcomes based on gene expression level(s) and correlation to the archive of FF and/or FFPE samples and historic outcomes associated therewith.

After creation of the profile data object, it is ready to receive various expression level information or data from a user or other source. In a preferred embodiment, expression level data from a test sample is introduced electronically and directly from a microarray reader. The expression profile data of a profile data object may be updated at anytime. Such an update will necessarily generate an updated profile data object, which may supersede and replace any previous object. Because the expression profile data is generated from expression level data that reflects unselected polyadenylated mRNA levels as provided by the present invention, the expression profile data is more complete and comprehensive. The invention can thus provide multiple gene sequences, the expression levels of which are associated with an outcome. The invention also allows subsets of an expression profile to be identified and correlated with an additional outcome.

In an alternative embodiment of the invention, the expression profile data may be adapted into a spreadsheet program for reviewing the profile data and optionally for comparison and analysis with expression data from a test sample. The program is preferably adapted to be capable of analyzing the expression data in comparison to the profile data to determine the outcome associated with the expression data. Other analysis modules (software) may be used or developed to utilize the adapted profile data to associate an outcome with a test sample.

The invention therefore provides a computer readable medium having a plurality of data fields stored on the medium and representing a data structure, such as expression data or expression profile data, comprising a first data field representing (expression or expression profile) data that is to be correlated or analyzed with input (outcome data or test sample expression data) information, said first data field being stored in a range of addresses in said computer readable medium; one or more receiver objects that will receive said input information, each receiver object being stored in a separate range of addresses in said computer readable medium, wherein each receiver object comprises a data field adapted for storing input information for correlation or analysis with said first data field.

In an alternative embodiment, the first data field is stored in a range of addresses used by one of the receiver objects. Moreover, the computer readable medium may optionally comprising a prompt field adapted for storing one or more data prompts to elicit entry of input information, which may be outcome information from a human patient from which an FFPE sample was obtained and used for generation of said expression data.

A preferred embodiment of the invention is a computer readable medium containing a gene expression profile comprising a plurality of data fields stored on the medium and representing a data structure and comprising at least one data field representing expression profile data stored in a range of addresses and a profile data receiver object that will receive gene expression data for correlation with said expression profile data. The receiver object is stored either in a separate range of addresses or in addresses that also store said at least one data field. The medium may optionally comprising a prompt field adapted for storing one or more data prompts to elicit entry of input information, which may be expression data from cells of a tissue sample from a human patient.

The present invention also provides a system and method for generating expression data for inclusion in a computer readable medium that optionally comprises a receiver object to receive outcome information for correlation with said data. The invention further provides a system and method for correlating said expression data with said outcome information such that expression level(s) of one or more gene sequences is/are associated or linked with said outcome. Moreover, the invention provides a system and method for generating a gene expression profile that is correlated with an outcome for inclusion in a computer readable medium. The medium optionally comprises a receiver object to receive test sample expression data for comparison and analysis with said gene expression profile. A system and method for said comparison and analysis is also provided. Preferably, the systems and methods of the invention are computer implemented and optionally stored as computer executable instructions on a computer readable medium.

As explained further below, the invention provides data structures or data sets comprising data that is to be used with information received by a receiver object. Embodiments of the invention include means for creating said data structures or data sets as well as said objects. Preferably, the data structures or data sets are created directly or indirectly via the analysis of gene expression as reflected in polyadenylated mRNA from FF and/or FFPE samples. The creation of gene expression data is an initial activity block of the invention. The activity may include the creation of prompts for input information as well as the creation of a receiver object to receive such information. A key feature of the invention is the use of expression data representing polyadenylated mRNA levels in combination with a receiver object as a central repository.

After receipt of input information, the next activity block is the correlation of said information with the expression level(s) of one or more gene sequences as found in the expression data. The results of the correlation are used as the data for additional data structures or data sets in the next activity block. The data structures or sets comprise gene expression profile data that is to be used with information received by one or more additional receiver objects. Means for creating said data structures or sets are also included in embodiments of the invention and are practiced as another activity of the invention. The activity may include the creation of prompts for input information as well as the creation of said receiver object(s) to receive such information. A key feature of the invention is the ability to use the expression profile data and input expression data from a test sample to predict the outcome of the subject from which the sample was obtained. The prediction is based upon the expression data (polyadenylated mRNA levels) from the FF and/or FFPE samples correlated with subject outcome(s) post sampling.

The prompts or a sequence of prompts that will be displayed to a user may be any that are appropriate to direct the entry of the requested information. Non-limiting examples related to outcome information include prompts for a disease or condition, as well as conditions that may be a subtype or stage thereof; treatment protocol(s) used; outcome of treatment(s); progress of the disease over time; survival time post sampling (based upon a relevant cause of death); and subsequent disease (e.g. metastatic cancer following a primary cancer). Non-limiting examples related to test sample expression data information include prompts for expression data (raw, processed or normalized); the microarray and probe sequences used; a suspected disease or condition; and type and/or age of sample. In one embodiment, the prompts are text fields that are displayed to the user. Generally, the information requested by the prompt is practically limited only by relevance to the task of expression profiling as disclosed herein. A variety of information can thus be requested by the prompts.

As described herein, receiver objects allows information received for correlation and analysis relative to expression data or expression profile data to be stored as part of the object. Thus, receiver objects contain data fields needed to store any appropriate information received. The receiver object may alternatively be part of an analysis object which is adapted to conduct correlation, analysis, and/or other comparison functions as described herein. Alternatively, and if an analysis module is to be used, the receiver objects may contain information that allows such an analysis module to extract relevant information and analyze or display such information for analysis by a user. Analysis is preferably conducted by any type of analysis module adapted for analyzing or comparing information received to expression data or expression analysis data.

In one embodiment, the analysis module is an adapted spreadsheet program which allows correlation, analysis and/or other comparison of the received information with said data. As a non-limiting example, the data may comprise a plurality of prompts that identify specific information items requested for use with the data. Each prompt may represent a row in a spreadsheet program and each information item received from the user may be placed in a column of the spreadsheet. A row may represent a particular outcome, such as sensitivity of a disease to a particular drug treatment, while the columns represent this outcome information for each FFPE sample used to generate the expression data to be used. The analysis module in this case would be adapted to correlate the outcome information with the expression level(s) of one or more gene sequences to construct a model as described herein.

Because the information received by the receiver object(s) must be communicated to the object(s), some embodiments of the invention comprise means for the communication of the information by electronic means. This may be conducted by a communications processor that is optionally directly linked to electronic devices (such as but not limited to databases containing outcome information or a microarray reader/analyzer/image processor) that contain the information to be communicated.

In another embodiment of the invention, an FF or FFPE expression information processing system is provided. The system is preferably computer implemented and comprises data fields and structures and optionally objects as described herein. The system preferably also comprises instructions for methods or procedures that processes expression data obtained from a microarray hybridization and stores it into a computer readable medium as described herein.

A further embodiment of the invention is a computer readable medium comprising instructions for a computer to store expression data, such as that from a microarray hybridization. The instructions preferably comprise generating the expression data from expression signal intensities from at least one microarray and storing at least one data set or structure containing the data. The instructions optionally include storing the instructions as well; storing the raw or processed or normalized data; or summarizing the expression data using a summarization method.

The invention also provides a system to store expression data or expression profile data comprising means for generating said data from hybridization signal intensities from one or more microarrays and/or means for storing said generated data.

Preferred expression data for the practice of the invention is derived from FFPE samples from subjects afflicted with a disease or unwanted condition wherein cells of a subject have aberrant or altered gene expression (including responses to infection such as by bacteria, mycobacteria and fungi). Non-limiting examples include cancer, viral infection, autoimmune diseases, arthritis, diabetes and other metabolic diseases.

Definitions of Terms Used Herein

A "sequence" or "gene sequence" as used herein is a nucleic acid molecule or polynucleotide composed of a discrete order of nucleotide bases. The term includes the ordering of bases that encodes a discrete product (i.e. "coding region"), whether RNA or proteinaceous in nature, as well as the ordered bases that precede or follow a "coding region". Non-limiting examples of the latter include 5' and 3' untranslated regions of a gene. It is appreciated that more than one polynucleotide may be capable of encoding a discrete product. It is also appreciated that alleles and polymorphisms of the disclosed sequences may exist and may be used in the practice of the invention to identify the expression level(s) of the disclosed sequences or the allele or polymorphism. Identification of an allele or polymorphism depends in part upon chromosomal location and ability to recombine during mitosis.

The terms "correlate" or "correlation" or equivalents thereof refer to an association between expression of one or more sequences and a physiologic state of a cell to the exclusion of one or more other states by use of the methods as described herein. The invention provides for the correlation between changes in gene sequence expression levels and outcomes and treatments encountered by subjects from whom an FFPE sample was obtained. Increases and decreases may be readily expressed in the form of a ratio between expression in a non-normal cell and a normal cell such that a ratio of one (1) indicates no difference while ratios of two (2) and one-half indicate twice as much, and half as much, expression in the non-normal cell versus the normal cell, respectively. The normal and non-normal cells are preferably from the same FFPE sample. Expression levels can be readily determined by quantitative methods as described below.

A "polynucleotide" is a polymeric form of nucleotides of any length, either ribonucleotides or deoxyribonucleotides linked by phosphodiester bonds and encompasses the strand of a given sequence as disclosed herein as well as the complementary strand of a given sequence. The term refers only to the primary structure of the molecule. Thus, this term includes double- and single-stranded DNA and RNA as well as analogs thereof comprising a non-phosphodiester backbone. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Amplification" may also be used in the context of DNA amplification wherein copies of coding sequences within the cellular genome are increased. "Multiple copies" mean at least 2 copies. A "copy" does not necessarily mean perfect sequence complementarity or identity to the template sequence. Methods for amplifying mRNA are generally known in the art, and include reverse transcription PCR (RT-PCR) and those described herein.

By corresponding is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990), J. Mol. Biol. 215:403-410 (using the published default setting, i.e. parameters w=4, t=17). Alternatively, RNA may be directly labeled as the corresponding cDNA by methods known in the art.

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm$^2$, more preferably at least about 100/cm$^2$, even more preferably at least about 500/cm$^2$ or at least about 1,000/cm$^2$. In some embodiments, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of probes in the array is known, the identities of a sample polynucleotides can be determined based on their binding to a particular position in the microarray.

Because the invention relies upon the identification of sequences that are over- or under-expressed, one embodiment of the invention involves determining expression by hybridization of mRNA, or an amplified or cloned version thereof, of a sample to a polynucleotide of a disclosed sequence. Preferred polynucleotides of this type contain at least about 20, at least about 22, at least about 24, at least about 26, at least about 28, at least about 30, at least about 32, at least about 34, at least about 36, at least about 38, at least about 40, at least about 42, at least about 44, or at least about 46 consecutive bases of a sequence that is not found in other human sequences. The term "about" as used in the previous sentence refers to an increase or decrease of 1 from the stated numerical value. Longer polynucleotides may of course contain minor mismatches (e.g. via the presence of mutations) which do not affect hybridization to the nucleic acids of a sample.

Such polynucleotides may be label to assist in their detection; alternatively, the nucleic acids to which such polynucleotides will hybridize may be labeled. Such polynucleotides may also be immobilized, such as by attachment to a solid support.

Even more preferred are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other sequences in the human genome. The term "about" as used in the preceding sentence refers to an increase or decrease of 10% from the stated numerical value. Preferably, the sequences are found in the 3' portion immediately upstream of the polyA tail of an expressed mRNA. The polynucleotides may of course contain minor mismatches which do not affect hybridization to the nucleic acids of a sample.

In another embodiment of the invention, all or part of a disclosed sequence may be amplified and detected by methods such as the polymerase chain reaction (PCR) and variations thereof, such as, but not limited to, quantitative PCR (QPCR), reverse transcription PCR (RT-PCR), and real-time PCR, optionally real-time RT-PCR. Such methods would utilize one or two primers that are complementary to portions of a disclosed sequence, where the primers are used to prime nucleic acid synthesis. The newly synthesized nucleic acids are optionally labeled and may be detected directly or by hybridization to a polynucleotide of the invention. The newly synthesized nucleic acids may be contacted with polynucleotides (containing sequences) of the invention under conditions which allow for their hybridization.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is a composition detectable by spectroscopic, photochemical, biochemical, immunochemical, electrical, optical or chemical means.

"Expression" and "gene expression" refers to transcription of nucleic acid material, such as the sequences of the invention, as well as the possibility that the transcribed sequences may be translated. The "level" of (gene) expression refers to the amount of expression, which may be increased or decreased relative to a control or normal level of expression. While increases and decreases may be readily determined by relative levels of mRNA production, decreases may also be determined by promoter status (such as methylation or other types of inactivation) of the sequences found to exhibit decreased expression.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present invention is based on increases and decreases in sequence expression, mutations in coding and non-coding regions of genes may also be assayed in the practice of the invention.

"Detection" or "detect" includes any means of detecting, including direct and indirect detection of gene expression and changes therein. For example, "detectably less" expression may be observed directly or indirectly, and the term indicates any reduction (including the absence of detectable signal). Similarly, "detectably more" product means any increase, whether observed directly or indirectly.

Oligo or poly dT sequences or primers refers to the presence of at least about 8 consecutive dT bases in a polynucleotide. Preferably, there are from about 8 to about 20, about 21 or about 30 consecutive dT bases. More than about 30 consecutive dT bases may also be used.

Random primers refers to the use of at least about 6 consecutive bases of random sequence as a primer for the synthesis of a nucleic acid strand. Preferably, the primers are of 6, 7, 8, 9, or 10 consecutive bases. As will be appreciated by the skilled person, primers that are too short will not be able to stably hybridize to a template strand to prime polynucleotide polymerization. Primers that are too long may not diffuse sufficiently fast to prime synthesis from a sufficient number of complementary sequences.

"Disease" refers to a change in the normal status of a living organism or a tissue or organ thereof that impairs the performance of the organism's physiological functions. A disease may be a result of exposure to environmental factors (such as, but not limited to, chemical agents or radiation), to an infective agent (such as, but not limited to, bacteria, viruses, or parasites), to congenital defects of the organism (such as, but not limited to, genetic mutations which may manifest in combination with environmental factors or at different times in the life of the organism). A disease may also be due to a combination of the above as well as descriptive of a set of related diseases. A non-limiting example of the latter is the use of the term "breast cancer" to refer to a group of cancer diseases in breast tissue as well as a group of subtypes of breast cancer.

Unless defined otherwise all technical and scientific terms used herein have the same meaning as commonly understood to one of ordinary skill in the art to which this invention belongs. The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Primers, oligonucleotides and polynucleotides employed in the present invention can be generated using standard techniques known in the art.

Having now generally described the invention, the same will be more readily understood through reference to the following examples which are provided by way of illustration, and are not intended to be limiting of the present invention, unless specified.

EXAMPLE 1

Selected Materials and Methods

Proteinase K Digestion Before Extracting RNA:

5-10 μm thick formalin-fixed paraffin embedded (FFPE) tissue sections mounted on frosted slides underwent deparaffinization, H&E staining and dehydration. Tissue lysates prepared from whole sections or laser captured cells of approximately 3000 to 5000 cells procured using the PixCell H system (Arcturus, Mountain View, Calif.) were treated with a solution comprised of 10 mM Tris pH 8.0, RNA-grade Proteinase K (100 or 500 μg/ml, Invitrogen, Carlsbad, Calif.), 2% SDS (Invitrogen, Carlsbad, Calif.) for at least 16 hours at 42° C.

Reverse TRANSCRIPTION:

To generate cDNA for either quantitative RT PCR analysis alone or for RNA amplification, demodified RNAs obtained from the samples were reverse transcribed using either oligo dT or random primers, in a reaction comprised of 50 mM Tris-HCl, 37.5 mM KCl, 1.5 mM $MgCl_2$. 10 mM DTT, 0.5 mM dNTPs (Pharmacia, Piscataway, N.J.), 40 units RNasin (Promega, Madison, Wis.), 200 units Superscript RT H (Invitrogen, Carlsbad, Calif.).

Brief Exemplar of RNA Amplification:

The mRNA component of each RNA preparation was linearly amplified using a modified version of the RiboAmp RNA amplification kit (Arcturus, Mountain View, Calif.). Briefly, the RNA from each sample was primed with 20 nanograms of an oligo dT primer containing a T7 promoter sequence, reverse transcribed and then converted to double stranded cDNA using random primers. The cDNA templates were then used in an in vitro transcription reaction using T7 RNA polymerase to generate amplified RNA (aRNA) in the antisense orientation (with sequences complementary to those of the mRNA used as a template for cDNA synthesis). A second round of amplification was performed to generate more aRNA, which was subsequently used as template to prepare fluorescently labeled cDNA probes for hybridization.

Probe Labeling and Microarray Hybridization:

A portion of the amplified RNA from each sample was used in a cDNA labeling reaction using 5-(3-aminoallyl)-2'-deoxyuridine-5'-triphosphate (aminoallyl-dUTP) using the Fair Play Kit (Stratagene, La Jolla, Calif.). Cy3 or Cy5 monoreactive dye (Amersham, Piscataway, N.J.) was conjugated onto purified cDNA and further purified using QiaQuick PCR Purification columns (Qiagen, Valencia, Calif.). To make fluorescently labeled cDNA, Cy5 dye was used for aRNAs from each test sample and Cy3 dye was used for a reference aRNA (Universal Human Reference RNA, Stratagene, La Jolla, Calif.). Equal amounts of purified, Cy5-labeled test sample cDNA was co-hybridized with Cy3-labeled reference cDNA to microarrays containing up to 22,000 features in a 400 hybridization solution (5×SSC, 0.1 WO COT-1 DNA, 0.2% SDS, 50% Formamide) at a probe concentration of 25 ng/μl for 17 hours at 42° C. in greater than 60% humidity.

Obtaining Expression Data:

After hybridization, microarray slides were washed, scanned and quantitated for hybridization signal intensity. Cy5 and Cy3 fluorescence intensities, after spot filtering/background correction and normalization, were expressed as normalized ratios of Cy5/Cy3 to represent the gene expression levels in the test samples with respect to the universal reference RNA.

EXAMPLE 2

RNA Stability in FFPE Samples and Amplification Thereof

5 μm tissue sections were formalin fixed for 1, 4 or 8 days and then paraffin embedded. The sections were deparaffinized, rehydrated with graded ethanols and then treated with Proteinase K at 500 μg/ml at 42° C. for 4 hours in 10 mM Tris-HCl pH 8.0; 2% SDS.

A frozen tissue sample was similarly digested with proteinase K for comparison.

FIG. 1 shows the results of RNA gel electrophoresis which shows that RNA from formalin fixed tissues remains intact in tissues fixed in formalin for 1 to 8 days. The samples were run in duplicate. "M" denotes an RNA marker lane.

Figure 2A:
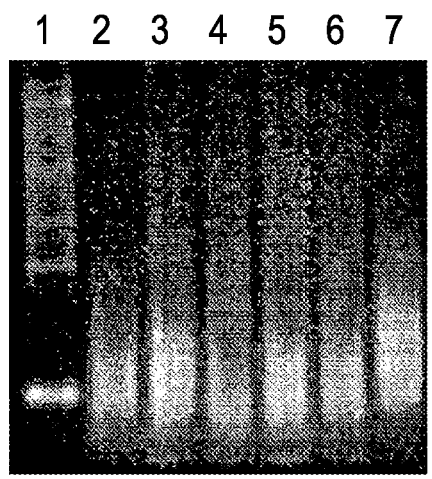
FIG. 2A shows RNA amplified from tissue samples fixed in formalin for 1, 4, or 8 days as well as fresh frozen tissue.

FIG. 2A shows the results of RNA amplification of the tissue samples fixed for 1, 4, or 8 days as well as fresh frozen tissue. The samples were proteinase K digested, followed by extraction using a GITC containing solution and purification on a silica column. The RNA was amplified as described above. Lanes 1-7 contain an RNA marker, 1 day FFPE, 1 day FFPE, 4 days FFPE, 8 days FFPE, 8 days FFPE, and 0 hour/fresh frozen, respectively.

Figure 2B:
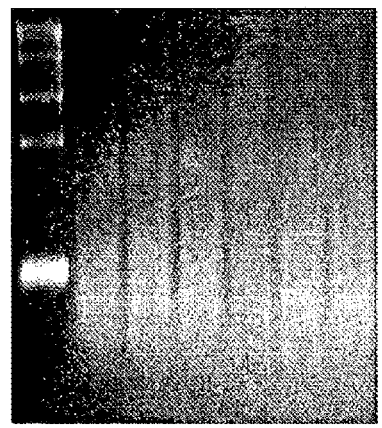
FIG. 2B shows additional results of tissue samples fixed for 4 days.

FIG. 2B shows the results of RNA amplification of tissue samples fixed for 4 days and analyzed in six lanes. The first lane contains RNA markers.

EXAMPLE 3

RNA Amplification from Archival Breast Cancer FFPE Samples

Figure 3A:
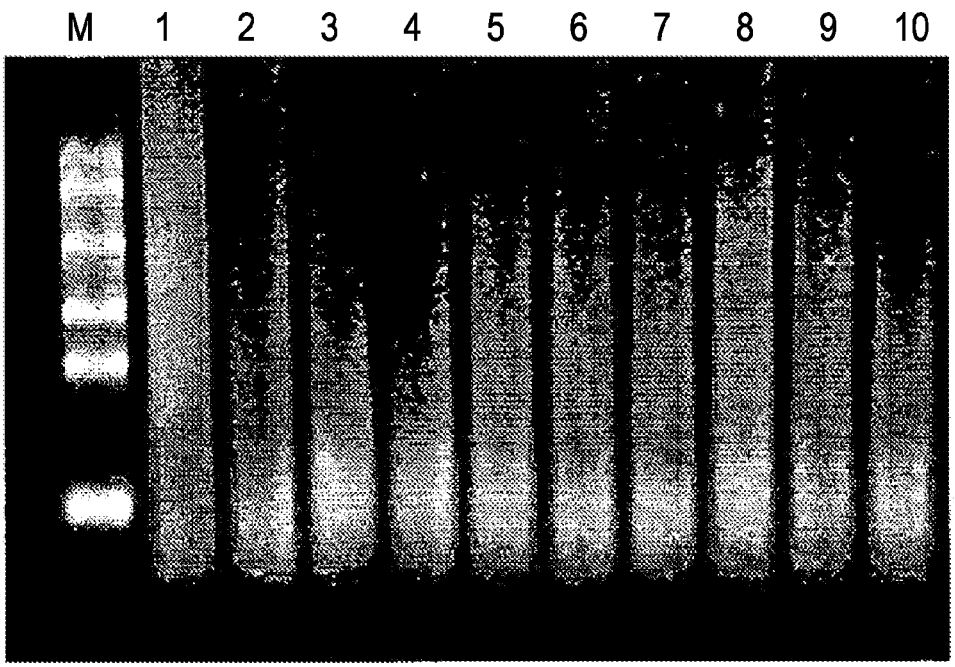
FIG. 3A shows RNA amplification from archival FFPE samples of about 1-2 years old.

Archival FFPE breast core biopsies of about 1 to 2 years old were treated as described above in Example 2. The following Table 1 summarizes the samples and the yield of amplified RNA therefrom. The results are shown in FIG. 3A, where M indicates RNA markers.

TABLE 1

| Lane | Year | Yield aRNA (μg) |
| --- | --- | --- |
| 1 | 2002 | 70.4 (did not work) |
| 2 | 2002 | 90.2 |
| 3 | 2002 | 98.4 |
| 4 | 2002 | 110.0 |
| 5 | 2002 | 93.7 |
| 6 | 2001 | 100.0 |
| 7 | 2001 | 90.2 |
| 8 | 2002 | 85.5 |
| 9 | 2002 | 87.9 |
| 10 | 2002 | 117.0 |

Figure 3B:
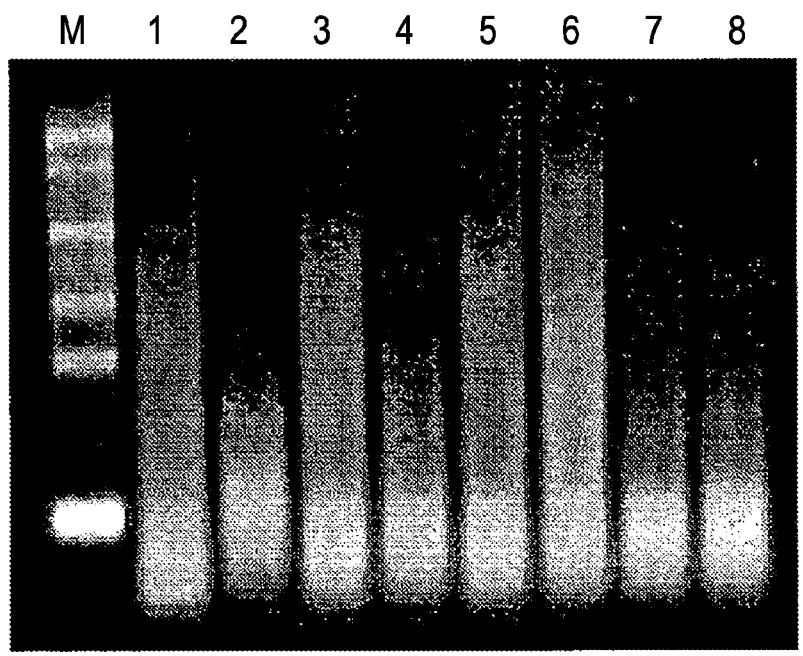
FIG. 3B shows the results of RNA amplification from four six year old archival FFPE breast core biopsies.

FIG. 3B shows the results of RNA amplification from four six year old archival FFPE breast core biopsies. The samples were analyzed in duplicate. The following Table 2 summarizes the samples and the yield of amplified RNA therefrom. "DCIS" refers to ductal carcinoma in situ; "IDC" refers to invasive ductal carcinoma.

TABLE 2

| Sample | Cellularity | Yield aRNA (μg) |
| --- | --- | --- |
| 1 | 30% DCIS | 106 |
| 2 | Same | 88 |
| 3 | 20% DCIS | 90 |
| 4 | Same | 131 |

TABLE 2-continued

| Sample | Cellularity | Yield aRNA (μg) |
|---|---|---|
| 5 | 40% IDC | 105 |
| 6 | Same | 121 |
| 7 | 50% DCIS | 117 |
| 8 | same | 127 |

EXAMPLE 4

RNA Amplification from Archival Bladder Cancer FFPE Samples

Archival FFPE human bladder samples of about 1 to 4 years old were treated as described above in Example 2. The following Table 3 summarizes the samples and the yield of amplified RNA therefrom. T1, Ta, HG, LG, and CIS, refer to superficially invasive, in situ papillary, high grade, low grade, and flat carcinoma in situ, respectively.

Figure 4:
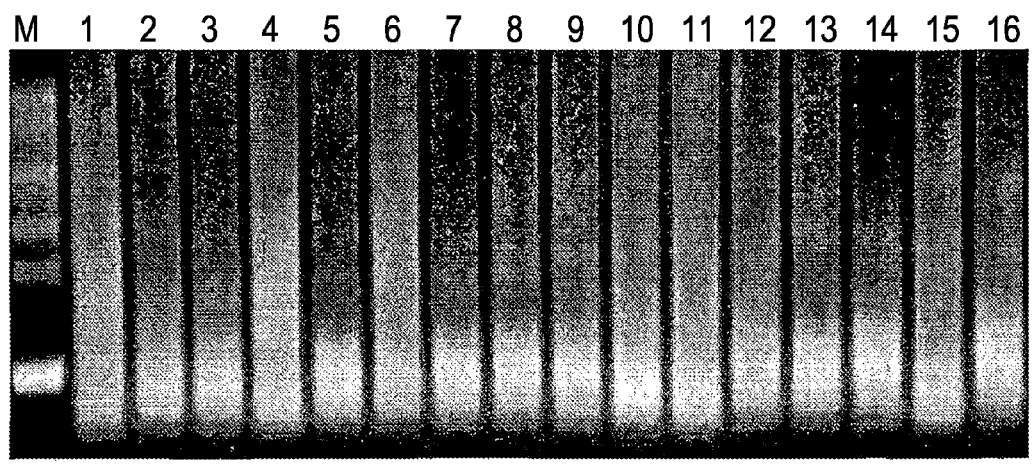
FIG. 4 shows RNA amplification from about 1 to 4 years old bladder cancer FFPE samples.

The results are shown in FIG. 4, where M indicates RNA markers. Lanes 1, 4, and 15 show the results of sub-optimal amplification.

TABLE 3

| Lane | Most advanced lesion | Block age at analysis (days) | Yield aRNA (μg) |
|---|---|---|---|
| 1 | T1 | 1650 | 74.64 |
| 2 | Ta (LG) | 1639 | 102.62 |
| 3 | Ta (HG) | 1602 | 93.79 |
| 4 | T1 | 1582 | 68.88 |
| 5 | Ta (HG) | 1181 | 112.13 |
| 6 | T1 | 1126 | 85.73 |
| 7 | Ta (HG) | 921 | 110.3 |
| 8 | CIS | 921 | 99.98 |
| 9 | T1 | 892 | 89.42 |
| 10 | Ta (HG) | 738 | 91.25 |
| 11 | CIS | 541 | 82.42 |
| 12 | CIS | 402 | 87.41 |
| 13 | T1 | 345 | 94.56 |
| 14 | CIS | 147 | 84.19 |
| 15 | T1 | 133 | 80.3 |
| 16 | T1 | 112 | 78.91 |

EXAMPLE 5

Consistency of Gene Expression in FFPE Samples

Figure 5:
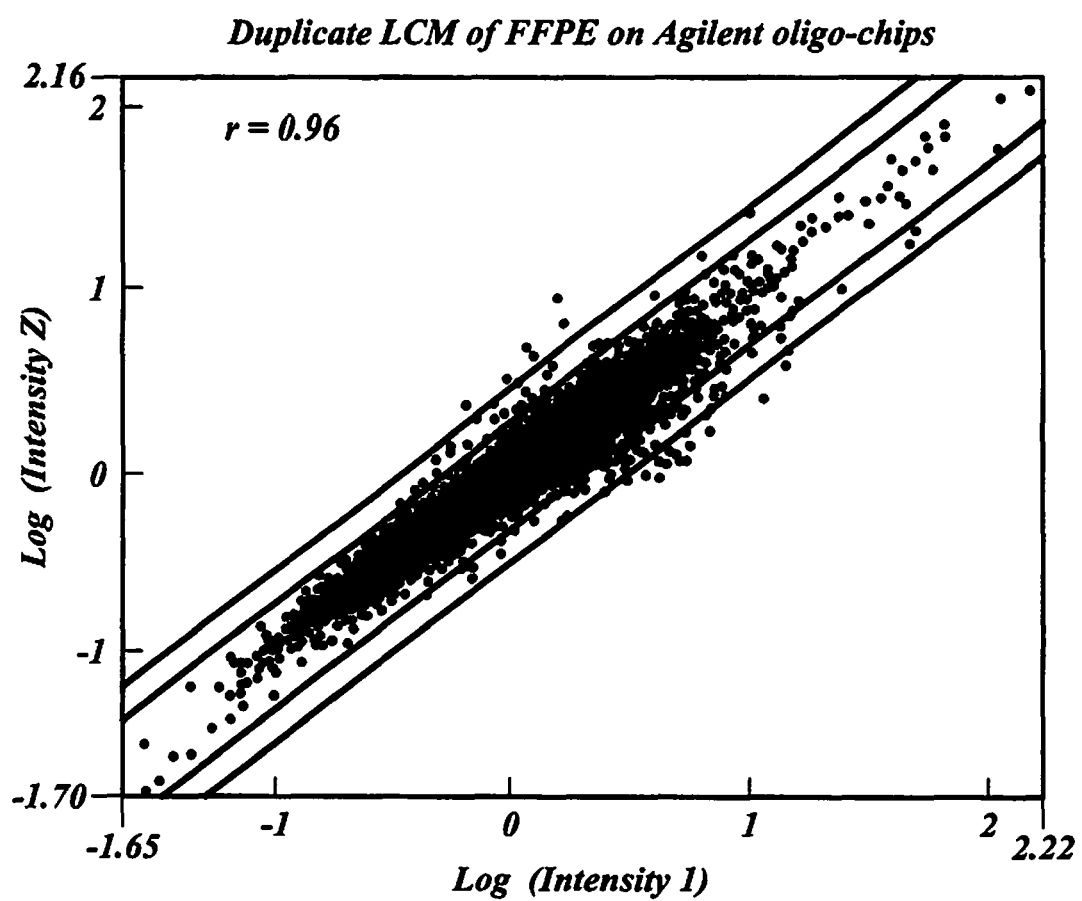
FIG. 5 shows a scatter-plot of signal intensities from two independent hybridizations of RNA amplified from an FFPE sample.

FFPE sample from a patient were used for two independent laser capture microdissection (LCM) followed by separate mRNA amplification as described in Example 2. The amplified RNA were used to generate labeled cDNA for hybridization of a microarray comprising 17296 oligonucleotide gene sequence probes. A scatter-plot of the (log) hybridization signal intensities for each probe from the two independent experiments are shown in FIG. 5. Only 148 genes (0.8% of total) showed over a 2-fold variation between the duplicate hybridizations. The overall correlation coefficient was 0.96.

EXAMPLE 6

Comparison of Gene Expression in FFPE and Frozen Samples

Figure 6:
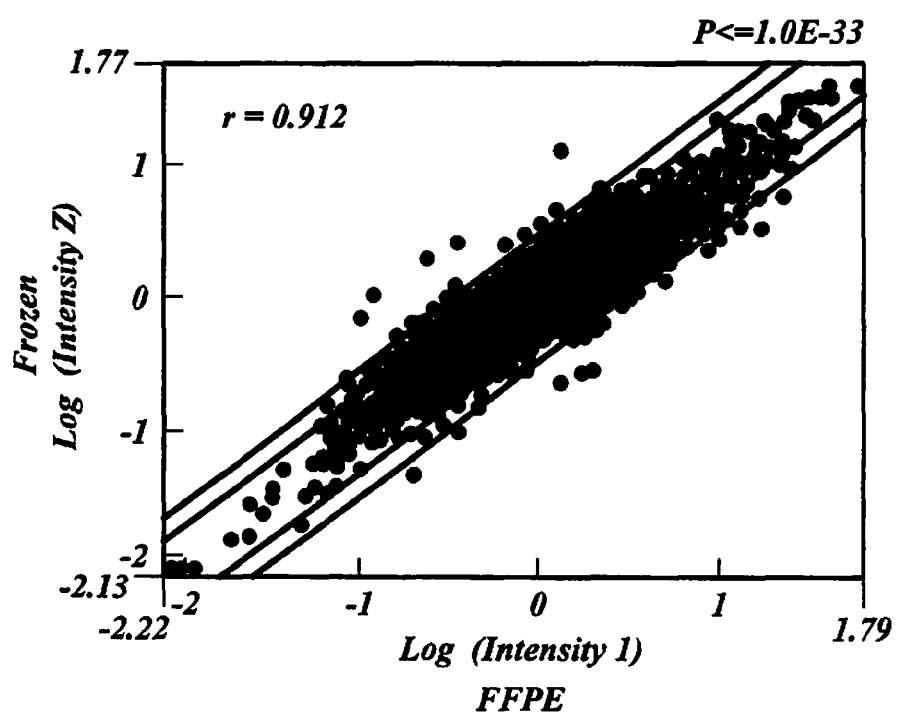
FIG. 6 shows a scatter-plot of signal intensities from an FFPE versus a frozen sample.

FFPE and frozen samples from the same patient biopsy were sectioned and used for mRNA amplification as described in Example 2 without laser capture microdissection. The amplified RNA were used to generate labeled cDNA for hybridization of a microarray. A scatter-plot of the (log) hybridization signal intensities for each probe sequence of the microarray from the FFPE and frozen samples are shown in FIG. 6. The overall correlation coefficient was 0.912.

Similar experiments with RNA amplified from paraffin embedded sections that have been fixed in formalin for 1, 4, or 8 days showed similar reproducibility of gene expression patterns. Correlations of intensities between such samples are shown in Table 4.

TABLE 4

|  | 1 day in formalin | 4 days in formalin |
|---|---|---|
| 4 days in formalin | r = 0.9212 |  |
| 8 days in formalin | r = 0.9328 | r = 0.9384 |

EXAMPLE 7

Demodification of RNA in FFPE Samples

Figure 7:
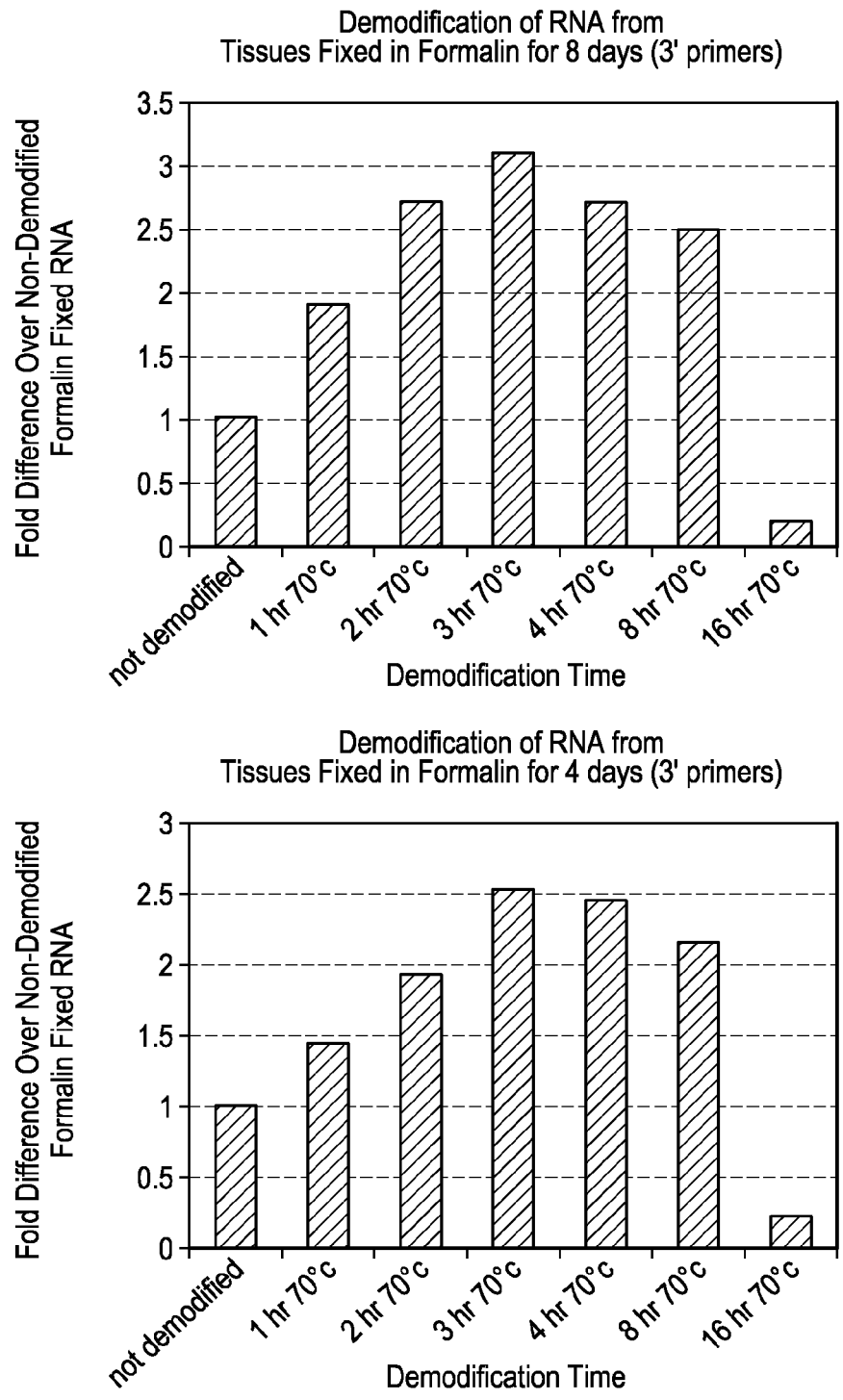
FIG. 7 shows the relative yield of RNA amplification of 3' sequences from FFPE samples fixed in formalin for various times after demodification with heat.

FFPE samples that were fixed in formalin for 4 or 8 days before embedding in paraffin were used for RNA extraction followed by demodification at 70° C. for various times. The samples were then amplified by RT-PCR using primers positioned to amplify about 110 bases upstream from the polyA site of the beta actin mRNA. The relative yield of the amplification is shown in FIG. 7, where demodification times of 3-8 hours gave good yields.

Figure 8:
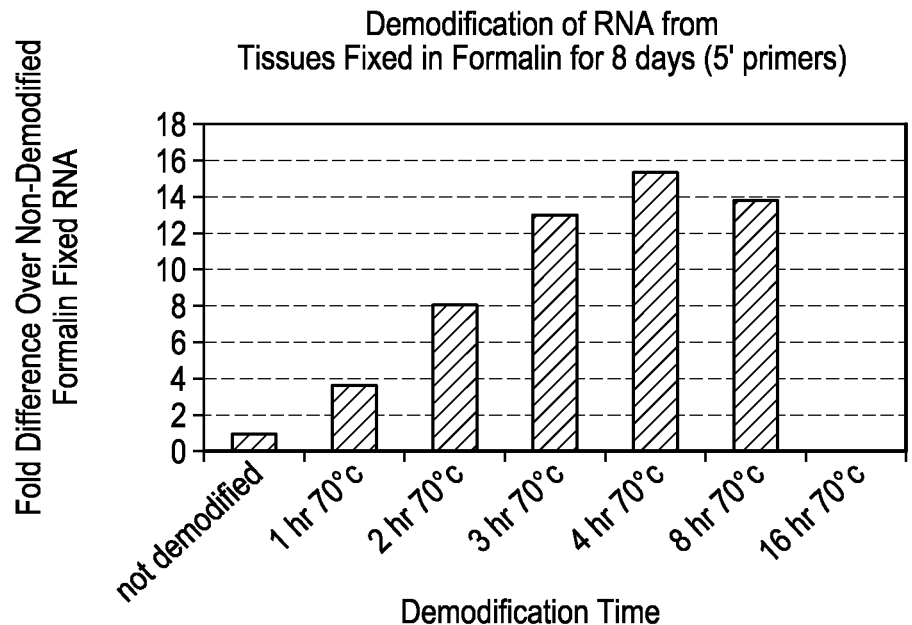
FIG. 8 shows the relative yield of RNA amplification of longer 3' sequences from FFPE samples fixed in formalin for various times after demodification with heat.
Figure 8:
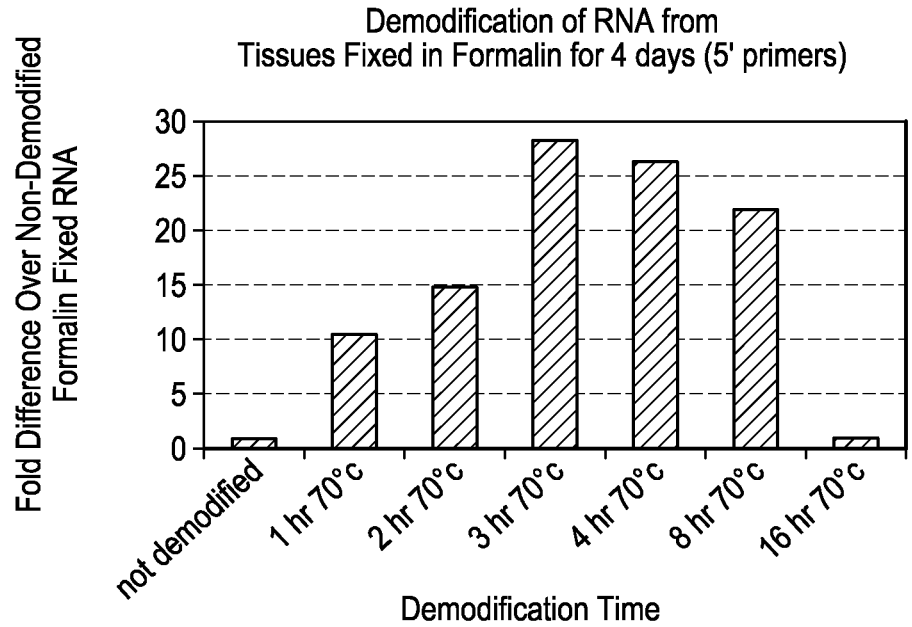

The samples were also amplified by RT-PCR using primers positioned to amplify about 1000 bases upstream from the polyA site of the beta actin mRNA. The relative yield of the amplification is shown in FIG. 8, where demodification times of 3-8 hours gave good yields.

Similar results were observed with FFPE samples that were fixed in formalin for 1 day before embedding.

EXAMPLE 8

Comparison of RNA Amplification Techniques

RNA from tissue fixed in formalin for 24 hours and subsequently paraffin embedded was used to prepare total RNA for amplification as described in Example 2. Total RNA was converted to double stranded cDNA (in a first round) using an oligo dT-T7 primer via use of exogenously supplied random primers to produce the second cDNA strand or by use of "endogenous priming" to produce the second cDNA strand without random primers. The product cDNA were used for ("first round") in vitro transcription (IVT) to produce amplified RNA that was used to produce cDNA in a second round using the same methods as the first round. The resultant cDNA was used for second round IVT, where biotin was incorporated into the amplified RNA product to generate aRNA probes for probe targets on a microarray.

Figure 9:
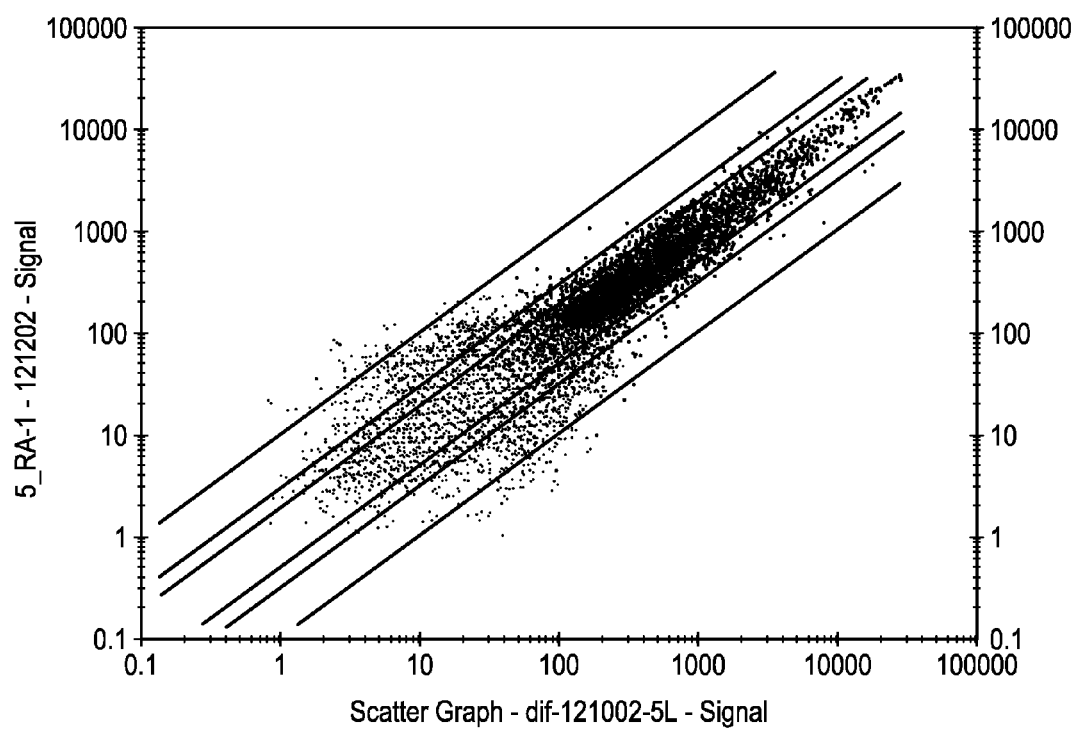
FIG. 9 shows a comparison of microarray data generated by use of amplified RNA prepared from cDNA prepared by the use of random primers or in the absence of random primers.

Prior to hybridization, 10-20 μg of biotinylated aRNA was fragmented in a buffer comprised of 20 mM Tris-acetate, pH 8.1, 50 mM KOAc, 15 mM MgOAc which was heated to 95° C. for 35 minutes and then chilled. The fragmented aRNA was subsequently purified and hybridized to microarrays at a concentration of 0.05 μg/μl, in a buffer comprised of 100 mM MES, 1M [Na+], 20 mM EDTA, 0.01% Tween-20, 0.1 mg/ml herring sperm DNA, 0.5 mg/ml acetylated BSA for 16 hours at 45° C. The resultant scatter graph showing the signal intensities at the microarray probe positions is shown in FIG. 9.

The X axis is without the use of random primers and the Y axis is with the use of random primers. The correlation coefficient r is 0.9173787, indicating that both methods are able to amplify RNA from an FFPE sample for use in the present invention.

REFERENCES

1. Beer et al, Gene Expression profiles predict survival of patients with lung adenocarcinoma., Nat. Med., 8, 816-824, 2002.
2. Wigle et al., Molecular Profiling of Non-Small Lung Cancer and Correlation with Disease-free Survival. Cancer Res., 62, 3005-3008, 2002.
3. Emmert-Buck et al., Laser Capture Microdissection. Science, 274, 998-1001, 1996.
4. Karsten et al., An evaluation of tyramide signal amplification and archived fixed and frozen tissue in microarray gene expression analysis. Nucleic Acid Research, 30, E4, 2002.
5. Lewis et al., Unlocking the archive-gene expression in paraffin-embedded tissue. J. Pathology, 195, 66-71, 2001.
6. Lehmann et al. Real-time PCR analysis of DNA and RNA extracted from formalin-fixed and paraffin-embedded biopsies. Methods, 25, 409-418, 2001.
7. Feldman, Reaction of formaldehyde with nucleotides and ribonucleic acid, Biochimica Et Biophysica Acta, 149, 20-34, 1967
8. Specht et al., Quantitative gene expression analysis in microdissected archival formalin-fixed and paraffin-embedded tumor tissue. American J. Pathology, 158, 419-429, 2001.
9. Cohen et al., Laser microdissection and gene expression analysis on formaldehyde-fixed archival tissue. Kidney International, 61, 125-132, 2002.
10. Masuda et al., Analysis of chemical modification of RNA from formalin-fixed samples and optimization of molecular biology applications for such samples. Nucleic Acids Research, 27, 4436-4443, 1999.
11. Danenberg et al. U.S. Pat. No. 6,428,963.
12. Wang et al. U.S. Pat. No. 5,672,696.
13. Chomczynski et al. Single-step method of RNA isolatin by acid guanidinium thiocyanate-phenol-chloroform extraction. Anal. Biochem. 162, 156-159, 1987.
14. Houze et al. Sonification as a means of enhancing the detection of gene expression levels from formalin-fixed, paraffin-embedded biopsies. Biotechniques 21, 1074-1082, 1996.
15. Su et al. High-throughput RT-PCR analysis of multiple transcripts using a microplate RNA isolation procedure. Biotechniques 6, 1107-1113, 1997.
16. Crino et al., Embryonic neuronal markers in tuberous sclerosis: single-cell molecular pathology. Proc. Natl. Acad. Sci., USA 93, 14152-14157, 1996.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for analysis of expressed RNA from cells of a deparaffinized FFPE (formalin fixed paraffin embedded) sample, said method comprising:
    indirectly labeling expressed RNA extracted from said cells of said deparaffinized FFPE sample, wherein indirectly labeling comprises synthesizing a plurality of first labeled cDNA strands complementary to said expressed RNA and synthesizing second cDNA strands that are complementary to said first cDNA strands, to form labeled nucleic acids; and
    detecting said expressed RNA after hybridization of the labeled nucleic acids to an array.
2. The method of claim 1 wherein said RNA is extracted from said cells by a method comprising
    obtaining a cell containing FFPE sample;
    treating said sample with proteinase K to produce material containing expressed RNA;
    removing said proteinase K and treating said material with DNase;
    removing said DNase to produce treated RNA.
3. The method of claim 1, further comprising heating said RNA extracted from said cells at about 70° C. before contacting said indirect labeling.
4. A method of comparing gene expression data from a subject to a gene expression profile, said method comprising:
    obtaining gene expression data from the subject by the method of claim 1,
    comparing said data to a gene expression profile generated by gene expression data from one or more FFPE samples from one or more other subjects, and
    determining whether said data is the same or similar as said gene expression profile.
5. The method of claim 1, wherein said cells are microdissected from said FFPE sample prior to RNA extraction.
6. The method of claim 1, wherein said FFPE sample is of a fine needle aspirate (FNA).
7. The method of claim 1, wherein said FFPE sample is of a core biopsy.
8. The method of claim 1, wherein said FFPE sample is of a needle biopsy.
9. The method of claim 1, wherein said deparaffinized FFPE sample comprises tumor tissue and the cells of said deparaffinized FFPE sample are tumor cells.
10. The method of claim 9, wherein said tumor tissue is of the pancreas, large intestine, kidney, lung, brain, or a lymphoma.
11. The method of claim 10, wherein said tumor tissue is pancreas tissue.
12. The method of claim 10, wherein said tumor tissue is large intestine tissue.
13. The method of claim 10, wherein said tumor tissue is kidney tissue.
14. The method of claim 10, wherein said tumor tissue is lung tissue.
15. The method of claim 10, wherein said tumor tissue is brain tissue.
16. The method of claim 10, wherein said tumor tissue is of a lymphoma.
17. The method of claim 1, wherein the array is a microarray.

* * * * *